(12) United States Patent
Schuler et al.

(10) Patent No.: US 12,004,805 B2
(45) Date of Patent: Jun. 11, 2024

(54) TISSUE MAPPING AND TREATMENT

(71) Applicant: SCHULER SCIENTIFIC SOLUTIONS, LLC, York, PA (US)

(72) Inventors: Brian Schuler, York, PA (US); David Bernstein, York, PA (US); David G. Matsuura, Solana Beach, CA (US); Phillip J. Simpson, Solana Beach, CA (US); Patricia Ellen Eisenhardt, San Clemente, CA (US)

(73) Assignee: SCHULER SCIENTIFIC SOLUTIONS, LLC, York, PA (US)

( * ) Notice: Subject to any disclaimer, the term of this patent is extended or adjusted under 35 U.S.C. 154(b) by 0 days.

(21) Appl. No.: 18/461,431

(22) Filed: Sep. 5, 2023

(65) Prior Publication Data
US 2023/0414278 A1 Dec. 28, 2023

Related U.S. Application Data

(63) Continuation of application No. 15/396,309, filed on Dec. 30, 2016, now Pat. No. 11,771,491.
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/00* (2013.01); *A61B 5/287* (2021.01); *A61B 5/6858* (2013.01);
(Continued)

(58) Field of Classification Search
CPC ..... A61B 18/1492; A61B 18/02; A61B 5/287; A61B 5/00; A61B 5/6858;
(Continued)

(56) References Cited

U.S. PATENT DOCUMENTS 3,326,207 A  6/1967 Egan
3,996,938 A  12/1976 Clark
(Continued)

FOREIGN PATENT DOCUMENTS

EP  0 771 547 A2  5/1997
EP  1 946 712 A1  7/2008
(Continued)

OTHER PUBLICATIONS

Franceschi, Frédéric, et al. "Phrenic nerve monitoring with diaphragmatic electromyography during cryoballoon ablation for atrial fibrillation: the first human application." Heart Rhythm 8.7 (2011): 1068-1071.
(Continued)

*Primary Examiner* — Michael F Peffley
*Assistant Examiner* — Bo Ouyang
(74) *Attorney, Agent, or Firm* — KNOBBE, MARTENS, OLSON & BEAR LLP

(57) ABSTRACT

Methods, systems, and devices are described for mapping and treating tissue during a medical procedure. In some cases, a device includes a mesh of wires with sensors coupled thereto. The device can be coupled to an expandable treatment element. The expandable treatment element can include multiple segments. The sensors can be used to map a tissue area and monitor the tissue during a medical procedure.

18 Claims, 19 Drawing Sheets

Related U.S. Application Data

(60) Provisional application No. 62/273,268, filed on Dec. 30, 2015.

(51) Int. Cl.
*A61B 5/287* (2021.01)
*A61B 18/02* (2006.01)
*A61B 18/00* (2006.01)
*A61M 25/09* (2006.01)

(52) U.S. Cl.
CPC .... *A61B 18/02* (2013.01); *A61B 2018/00041* (2013.01); *A61B 2018/0022* (2013.01); *A61B 2018/00267* (2013.01); *A61B 2018/00351* (2013.01); *A61B 2018/00577* (2013.01); *A61B 2018/00642* (2013.01); *A61B 2018/00791* (2013.01); *A61B 2018/00839* (2013.01); *A61B 2018/00982* (2013.01); *A61B 2018/0212* (2013.01); *A61M 25/09* (2013.01)

(58) Field of Classification Search
CPC .. A61B 2018/00041; A61B 2018/0022; A61B 2018/00267; A61B 2018/00351; A61B 2018/00577; A61B 2018/00642; A61B 2018/00791; A61B 2018/00839; A61B 2018/00982; A61B 2018/0212; A61M 25/09
See application file for complete search history.

(56) References Cited

U.S. PATENT DOCUMENTS

| | | |
|---|---|---|
| 4,304,239 A | 12/1981 | Perlin |
| 4,519,403 A | 5/1985 | Dickhudt |
| 4,552,127 A | 11/1985 | Schiff |
| 4,649,924 A | 3/1987 | Taccardi |
| 4,660,571 A | 4/1987 | Hess et al. |
| 4,699,147 A | 10/1987 | Chilson et al. |
| 4,776,349 A | 10/1988 | Nashef et al. |
| 4,824,435 A | 4/1989 | Giesy et al. |
| 4,921,484 A | 5/1990 | Hillstead |
| 4,940,064 A | 7/1990 | Desai |
| 5,156,151 A | 10/1992 | Imran |
| 5,222,501 A | 6/1993 | Ideker et al. |
| 5,255,678 A | 10/1993 | Deslauriers |
| 5,263,493 A | 11/1993 | Avitall |
| 5,277,207 A | 1/1994 | Stern et al. |
| 5,311,866 A | 5/1994 | Kagan et al. |
| 5,313,943 A | 5/1994 | Houser et al. |
| 5,345,936 A | 9/1994 | Pomeranz et al. |
| 5,411,025 A | 5/1995 | Webster, Jr. |
| 5,690,642 A | 11/1997 | Osborne et al. |
| 5,860,974 A | 1/1999 | Abele |
| 5,891,136 A | 4/1999 | McGee et al. |
| 5,972,026 A | 10/1999 | Laufer et al. |
| 6,053,913 A | 4/2000 | Tu et al. |
| 6,142,993 A | 11/2000 | Whayne et al. |
| 6,240,307 B1 | 5/2001 | Beatty et al. |
| 6,475,179 B1 | 11/2002 | Wang et al. |
| 6,529,756 B1* | 3/2003 | Phan .................. A61B 18/1492 606/49 |
| 6,748,255 B2 | 6/2004 | Fuimaono et al. |
| 6,899,726 B2 | 5/2005 | Larnard et al. |
| 6,970,730 B2 | 11/2005 | Fuimaono et al. |
| 7,149,563 B2 | 12/2006 | Fuimaono et al. |
| 7,236,821 B2 | 6/2007 | Cates et al. |
| 7,371,231 B2 | 5/2008 | Rioux et al. |
| 7,567,841 B2 | 7/2009 | Chan |
| 7,569,052 B2 | 8/2009 | Phan et al. |
| 7,691,119 B2 | 4/2010 | Farnan |
| 7,722,604 B2 | 5/2010 | Brown, III et al. |
| 7,959,627 B2 | 6/2011 | Utley et al. |
| 8,187,266 B2 | 5/2012 | Dickens et al. |
| 8,398,624 B2 | 3/2013 | Rioux et al. |
| 8,702,694 B2 | 4/2014 | Wallace et al. |
| 9,060,756 B2 | 6/2015 | Bencini et al. |
| 9,179,970 B2 | 11/2015 | Utley et al. |
| 9,381,361 B2 | 7/2016 | Giovangrandi et al. |
| 10,945,780 B2 | 3/2021 | Lalonde |
| 2001/0029366 A1 | 10/2001 | Swanson et al. |
| 2002/0107511 A1* | 8/2002 | Collins .............. A61B 18/1492 606/41 |
| 2003/0069606 A1 | 4/2003 | Girouard et al. |
| 2003/0135233 A1 | 7/2003 | Bates et al. |
| 2003/0236495 A1 | 12/2003 | Kennedy |
| 2004/0078036 A1 | 4/2004 | Keidar |
| 2004/0082947 A1 | 4/2004 | Oral et al. |
| 2004/0092787 A1 | 5/2004 | Hughett et al. |
| 2004/0106896 A1 | 6/2004 | Lee et al. |
| 2004/0143256 A1 | 7/2004 | Bednarek |
| 2004/0254621 A1 | 12/2004 | Jones et al. |
| 2005/0049585 A1 | 3/2005 | Fleischman et al. |
| 2005/0171525 A1* | 8/2005 | Rioux ................ A61B 18/1492 606/41 |
| 2008/0281391 A1 | 11/2008 | Macadam et al. |
| 2009/0299355 A1 | 12/2009 | Bencini et al. |
| 2010/0160906 A1 | 6/2010 | Jarrard |
| 2011/0034912 A1* | 2/2011 | de Graff ........... H01L 27/14687 606/41 |
| 2012/0101413 A1 | 4/2012 | Beetel et al. |
| 2013/0030425 A1* | 1/2013 | Stewart .................. A61B 18/02 606/41 |
| 2013/0035576 A1 | 2/2013 | O'Grady et al. |
| 2013/0184706 A1* | 7/2013 | Gelbart ................ A61B 5/6858 606/41 |
| 2013/0261471 A1 | 10/2013 | Saha et al. |
| 2014/0046320 A1* | 2/2014 | Kappel .............. A61B 18/1492 606/49 |
| 2014/0142570 A1 | 5/2014 | Bakczewitz et al. |
| 2015/0005762 A1 | 1/2015 | Belk et al. |
| 2015/0057563 A1* | 2/2015 | Kowalski ............... A61B 5/389 600/554 |
| 2015/0105770 A1 | 4/2015 | Amit |
| 2015/0250399 A1 | 9/2015 | Laughner et al. |
| 2015/0359487 A1 | 12/2015 | Coulombe |
| 2016/0287323 A1 | 10/2016 | Yagi et al. |
| 2017/0143415 A1* | 5/2017 | Laughner ............... A61B 90/37 |
| 2017/0189106 A1 | 7/2017 | Schuler et al. |
| 2021/0177509 A1 | 6/2021 | Schuler et al. |
| 2021/0236816 A1 | 8/2021 | Waldstreicher et al. |

FOREIGN PATENT DOCUMENTS

| | | |
|---|---|---|
| WO | WO 2000/051683 | 9/2000 |
| WO | WO 2009/129484 | 10/2009 |
| WO | WO 2017/117582 | 7/2017 |
| WO | WO 2018/212840 | 11/2018 |
| WO | WO 2021/119479 | 6/2021 |
| WO | WO 2023/114991 | 6/2023 |

OTHER PUBLICATIONS

Okishige, Kaoru, et al. "Quick, safe, and effective maneuver to prevent phrenic nerve injury during cryoballoon ablation of atrial fibrillation." Journal of Interventional Cardiac Electrophysiology 53 (2018): 233-238.

* cited by examiner

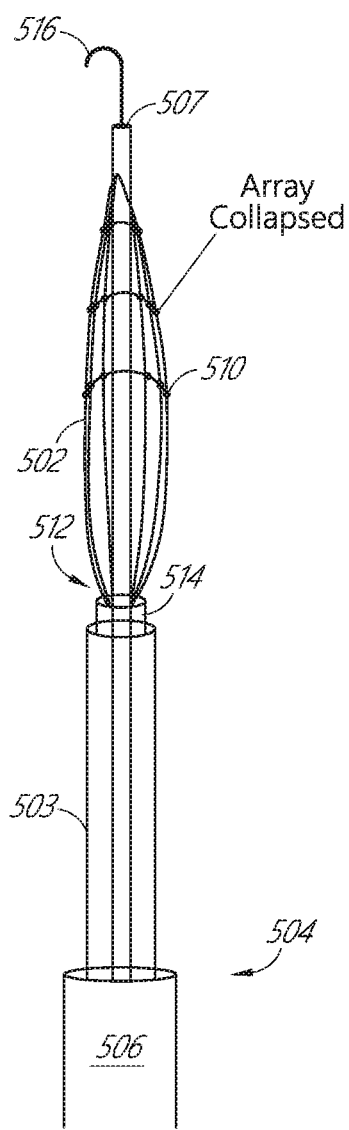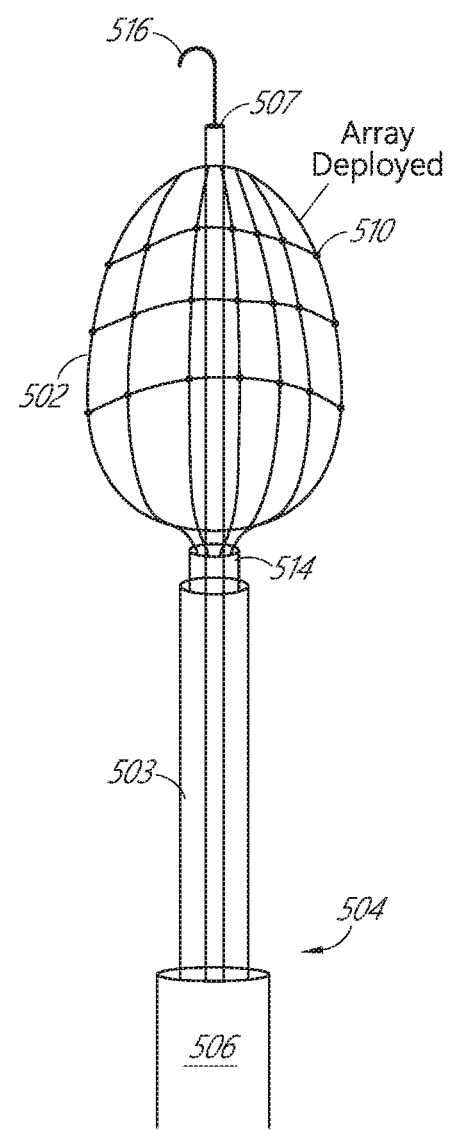
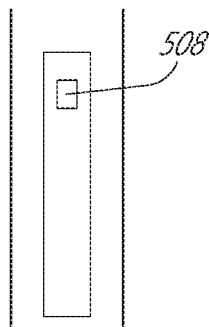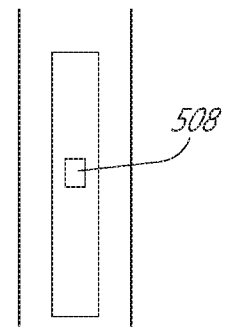
FIG. 5A    FIG. 5B

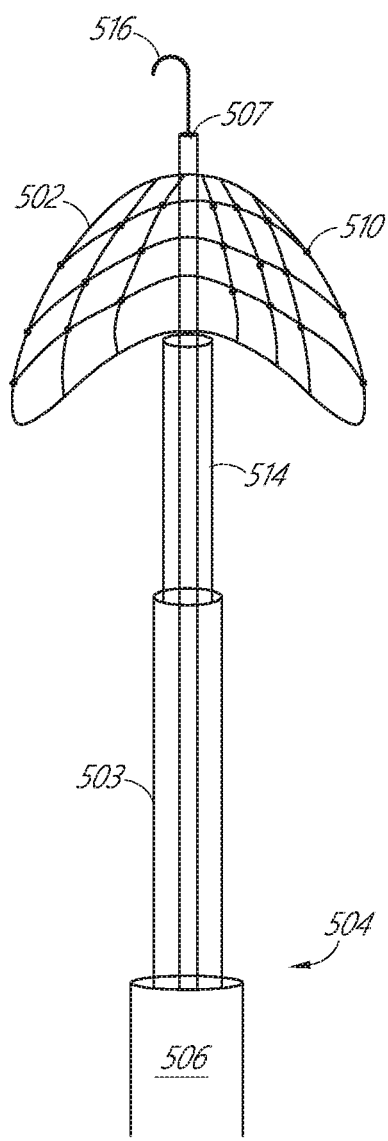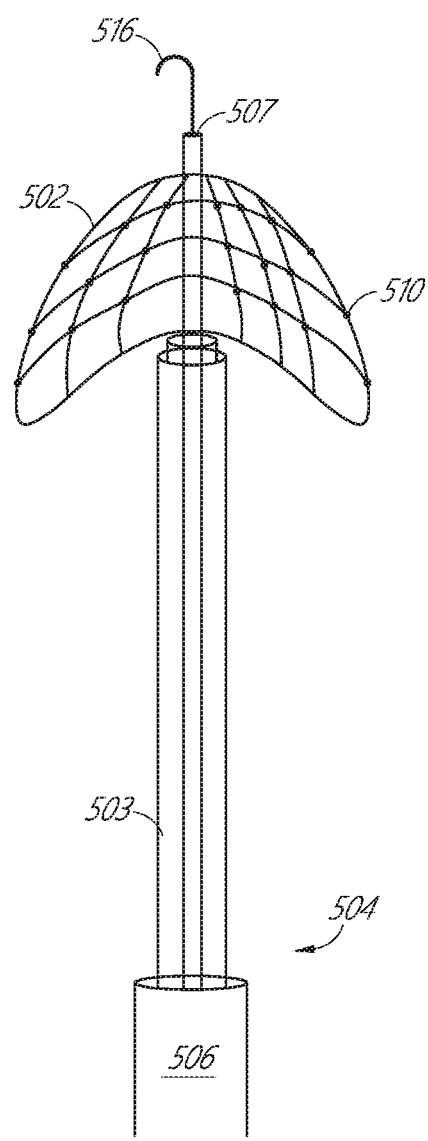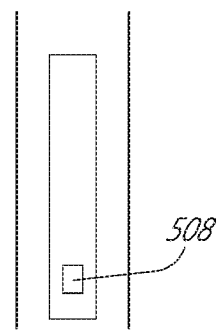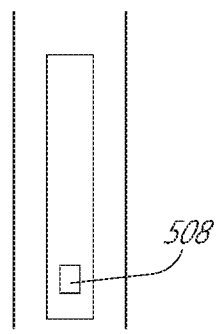
FIG. 5C　　　　　　　　　　FIG. 5D

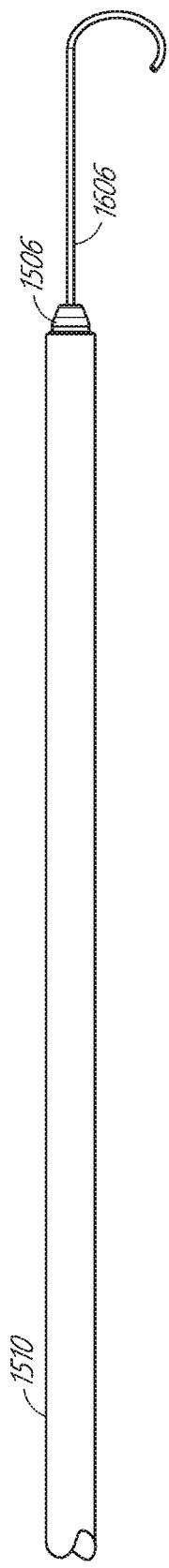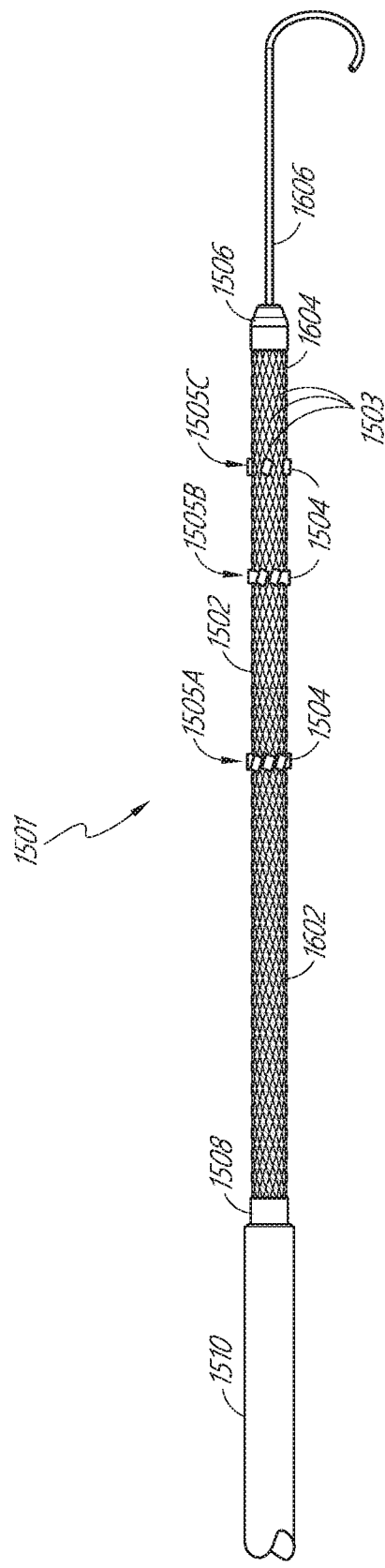
FIG. 16A
FIG. 16B

TISSUE MAPPING AND TREATMENT

INCORPORATION BY REFERENCE

The present application is a continuation application of U.S. application Ser. No. 15/396,309, filed Dec. 30, 2016, which claims priority benefit to U.S. Prov. App. No. 62/273,268, filed Dec. 30, 2015, entitled PHRENIC NERVE LOCATION AND INJURY PREVENTION, which is incorporated herein in its entirety.

BACKGROUND

In many medical procedures, catheters are used to treat tissue.

BRIEF DESCRIPTION OF THE DRAWINGS

FIGS. 5A, 5B, 5C, 5D are diagrams illustrating embodiments of a complementary mapping device and treatment device in different configurations and positions

FIGS. 16A-16C are diagrams illustrating embodiments of a mapping overlay and a treatment device in different configurations and positions.

DETAILED DESCRIPTION

Figure 1:
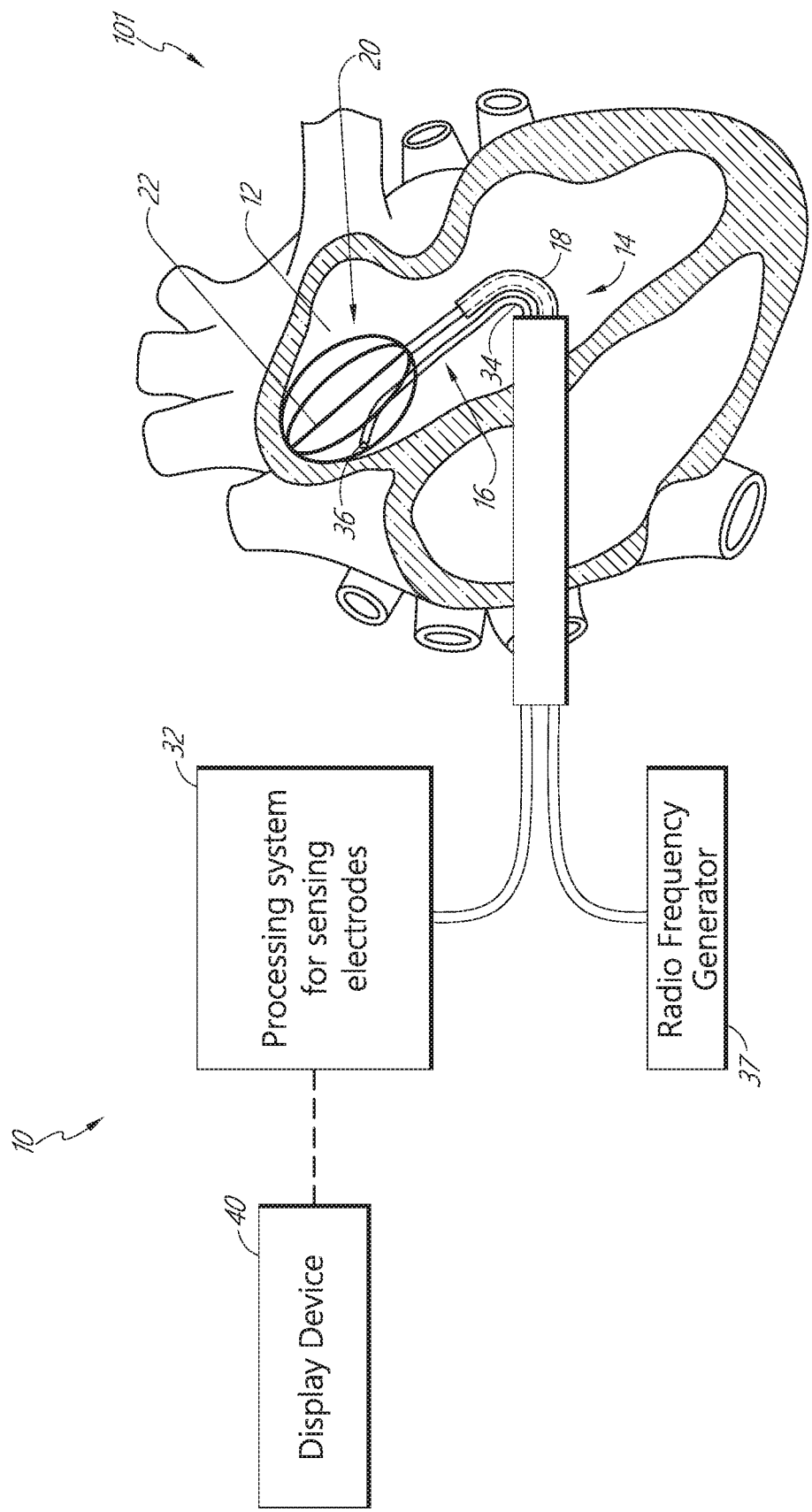
FIG. 1 is a diagram illustrating an embodiment of a treatment system.

During medical procedures using catheters, it can be difficult to identify tissue proximate to the catheter. Furthermore, in some cases, when the tissue is being treated it can be difficult to monitor the effects of the treatment on tissue proximate the tissue that is to be treated. A method and device described herein can be used as part of or in conjunction with a treatment device to map tissue at or near a target site and monitor the tissue at or near the target site during treatment. In same embodiments, the device can be used in conjunction with a treatment device used to treat cardiac arrhythmia. However, it will be understood that the methods and device described herein can be used with many types of treatment devices.

Cardiac Arrhythmia

Cardiac arrhythmia, a condition in which the heart's normal rhythm is disrupted, includes many different forms. For example, cardiac arrhythmia includes premature atrial contractions (PACs), atrial flutter, accessory pathway tachycardias, atrial fibrillation, atrioventricular (AV) nodal reentrant tachycardia (AVNRT), premature ventricular contractions (PVCs), ventricular tachycardia (VT), ventricular fibrillation, long QT syndrome, and bradyarrhythmias.

Certain types of cardiac arrhythmias, including atrial fibrillation (AF), may be treated by ablation (for example, radiofrequency (RF) ablation, cryoablation, ultrasound ablation, laser ablation, and the like), either endocardially or epicardially.

As mentioned above, one method of ablating tissue of the heart and pulmonary veins to control atrial fibrillation includes delivering radiofrequency (RF) energy to the tissue to be ablated. In particular, high frequency energy can be employed, for example, to cause ionic agitation and frictional heat in targeted tissue, causing permanent damage to the tissue. Once damaged, the tissue may no longer propagate or source electrical signals, and the fibrillation may be treated or reduced. The RF energy can be delivered by an RF catheter having an RF source at a distal treatment end that is positioned at a target site inside a patient during a treatment procedure.

Another method of ablating tissue of the heart and pulmonary veins to control atrial fibrillation is through cryotherapy, or the extreme cooling of body tissue. Cryotherapy may also cause permanent alteration to treated tissue, preventing the treated tissue from propagating or sourcing electrical signals, thereby reducing or eliminating atrial fibrillation. Cryotherapy may be delivered to appropriate target sites inside a patient's heart and circulatory system by a cryotherapy catheter. A cryotherapy catheter can include a treatment member at its distal end, such as an expandable balloon having a cooling chamber inside. A cryotherapy agent can be provided by a source external to the patient at the proximal end of the cryotherapy catheter and delivered distally through a lumen in an elongate member to the cooling chamber where it is released. Release of the cryotherapy agent into the chamber cools the chamber, the balloon's outer surface, and tissue that is in contact with the outer surface, to perform ablation. The cryotherapy agent may be exhausted proximally through an exhaust lumen in the elongate member to a reservoir external to the patient.

Furthermore, in the case of cryoballoon ablation, the distal hemisphere of the balloon contacts the pulmonary vein antrum in an occlusive manner. Tissue in contact with distal hemisphere of the cryoballoon will be ablated as liquid N2O evaporates in the distal balloon. As the tissues freezes, a shell of ice forms around the balloon and penetrates full thickness through the wall of the pulmonary vein antrum reaching extracardiac tissues. This can include non-targeted tissues such as the phrenic nerve, esophagus and vagus nerve. The same non-targeted tissues can also be damaged by other balloon directed therapies including but not limited to radiofrequency hot balloon, high frequency ultrasound balloon and laser balloon.

Phrenic Nerve Injury

One possible complication of an ablation procedure is damage to the phrenic nerves, which are involved in breathing and both receive and transmit nerve signals to the diaphragm. Phrenic nerve injury (PNI) can cause dyspnea, cough, hiccup, and/or sudden diaphragmatic elevation. The majority of patients with PNI recover over time, such as within days or months, but PNI may be persistent in a minority of patients.

The main function of the phrenic nerves is to control breathing by acting on the diaphragm. As such, it is possible to monitor phrenic nerve viability by stimulating the phrenic nerves electrically and detecting the corresponding physiologic response. Means for detecting physiologic response may include electromyography (the detection of electromyograms such as compound motor action potentials, or electrical potential generated by muscle cells when the cells are electrically or neurologically activated), mechanomyography (the detection of mechanomyograms, or mechanical signals observable from the surface of a muscle when the muscle is contracted), and kinemyography (the detection of electrical currents generated after deformation of a mechanosensor), auditory cardiotocography (detection of sound waves created by the diaphragmatic contraction). One can also directly observe the diaphragmatic movement fluoroscopically in a spontaneously breathing patient. Pacing of the nerve and palpation of the intensity of the diaphragmatic contraction can also be used to monitor the function of the nerve if the pacing source is positioned distal to the ablation source in the case of balloon cryoablation.

In some embodiments, to avoid phrenic nerve injury (PNI), the electrical activity of a pulmonary vein (or other target site) can be mapped prior to permanent ablation by either RF, high-frequency ultrasound (HIFU), laser, hot balloon, and/or cryotherapy, in order to pinpoint appropriate ablation target sites. Some apparent target sites may have non-targeted tissues such as the phrenic nerve or esophagus in close proximity and ablation at those sites may cause collateral damage such as injury to the phrenic nerve as the ablation penetrates deeper into the tissues. Treating other target sites may affect healthy tissue in undesirable ways (e.g., creating conduction blocks). Precisely mapping the electrical activity in a target treatment region can help focus the treatment and confirm its efficacy and safety.

Mapping Catheter

Various specialized mapping catheters may be employed to electrically map tissue, such as a circular catheter or a multi-electrode basket catheter. As a non-limiting example, in some embodiments, the Constellation catheter, available from Boston Scientific, can be used to electrically map tissue.

Such mapping catheters can be positioned at possible target sites inside a patient, and electrodes at those sites can provide signals to a processing system external to the patient that can process the signals and provide physicians with information to subsequently position a separate RF, HIFU, laser, hot balloon, or cryotherapy catheter and deliver with that separate catheter appropriately targeted ablation energy. In some cases, the mapping catheters can be used to pace and map the phrenic nerve as well.

With reference to FIG. 1 below, system 10 can include a mapping catheter 14 and an ablation catheter 16. Each probe 14/16 can be separately introduced into target region 12 through a vein or artery (e.g., the femoral vein or artery) using a suitable percutaneous access technique. Alternatively, mapping catheter 14 and ablation catheter 16 can be assembled in an integrated structure for simultaneous introduction and deployment in target region 12. However, it will be understood that in some embodiments, the system 10 can omit the ablation catheter 16.

Mapping catheter 14 can include a catheter shaft 18. The distal end of the catheter shaft 18 can include mapping device 20, which can include a three-dimensional multiple electrode structure 20. Mapping device 20 can take the form of a basket having a plurality of struts 22 (see FIG. 2), although other multiple electrode structures could be used. A plurality of mapping electrodes 24 (not explicitly shown on FIG. 1, but shown on FIG. 2) can be disposed along struts 22. Each electrode 24 can be configured to sense intrinsic physiological activity in the anatomical region. In some embodiments, electrodes 24 can be configured to detect activation signals of the intrinsic physiological activity within the anatomical structure (e.g., the activation times of cardiac activity).

Electrodes 24 can be electrically coupled to a processing system 32. A signal wire (not shown) can be electrically coupled to each electrode 24 on mapping device 20. The wires can extend through shaft 18 and electrically couple each electrode 24 to an input of processing system 32. Electrodes 24 can sense electrical activity in the anatomical region (e.g., myocardial tissue). The sensed activity (e.g., activation signals) can be processed by processing system 32, which can assist the physician by generating an electrical activity map (e.g., a vector field map, an activation time map, etc.) to identify the site or sites within the heart appropriate for a diagnostic and/or treatment procedure. For example, processing system 32 can identify a near-field signal component (e.g., activation signals originating from cellular tissue adjacent to the mapping electrode 24) or from an obstructive far-field signal component (e.g., activation signals originating from non-adjacent tissue). The near-field signal component can include activation signals originating from atrial myocardial tissue whereas the far-field signal component can include activation signals originating from ventricular myocardial tissue. The near-field activation signal component can be further analyzed to find the presence of a pathology and to determine a location suitable for ablation for treatment of the pathology (e.g., ablation therapy).

Processing system 32 can include dedicated circuitry (e.g., discrete logic elements and one or more microcontrollers; a memory or one or more memory units, application-specific integrated circuits (ASICs); and/or specially configured programmable devices, such as, for example, programmable logic devices (PLDs) or field programmable gate arrays (FPGAs) for receiving and/or processing the acquired activation signals. In at least some embodiments, processing system 32 includes a general-purpose microprocessor and/or a specialized microprocessor (e.g., a digital signal processor, or DSP, which can be optimized for processing activation signals) that executes instructions to receive, analyze and display information associated with the received activation signals. In such implementations, processing system 32 can include program instructions, which when executed, perform part of the signal processing. Program instructions can include, for example, firmware, microcode or application code that is executed by microprocessors or microcontrollers. The above-mentioned implementations are merely exemplary. A variety of processing systems 32 are contemplated.

In some embodiments, processing system 32 can be configured to measure the electrical activity in the myocardial tissue adjacent to electrodes 24. For example, in some embodiments, processing system 32 can be configured to detect electrical activity associated with a dominant rotor or divergent activation pattern in the anatomical feature being mapped. Dominant rotors and/or divergent activation patterns can have a role in the initiation and maintenance of atrial fibrillation, and ablation of the rotor path, rotor core, and/or divergent foci can be effective in terminating the atrial fibrillation. In either situation, processing system 32 processes the sensed activation signals to generate a display of relevant characteristics, such as an isochronal map, activation time map, action potential duration (APD) map, a vector field map, a contour map, a reliability map, an electrogram, a cardiac action potential, and/or the like. The relevant characteristics can be used by the physician to identify a site suitable for ablation therapy.

Additionally, the electrodes 24 of the mapping catheter 14 can be used to pace and map the phrenic nerve. For example, one or more of the electrodes 24 can be activated. If the activated electrode 24 is within a threshold distance of the phrenic nerve it can activate it. In some cases, when paced, the phrenic nerve can cause the diaphragm to contract. Furthermore, as the proximity between the activated electrode and phrenic nerve increases, the strength of the contraction of the diaphragm can increase. Based on which electrodes 24 pace the phrenic nerve, all or portions of the phrenic nerve can be located. In some cases, to locate the phrenic nerve, the electrodes 24 can be activated (sequentially or otherwise) along a tine and/or in a circumference on the different tines. In certain embodiments when mapping in a circumference, once one circumference of electrodes is activated 24 a next circumference of electrodes can be activated (e.g., sequentially or otherwise). The next circumference can either be distal or proximal to the atrium with respect to the previous circumference (e.g., the activated circumference can move proximal-to-distal or vice versa).

In some embodiments, the portion of the phrenic nerve that is proximal (in some embodiments, the most proximal) to the atrium can be identified. In some cases, the determined location of the phrenic nerve (or portions thereof) can be displayed on a corresponding display. As will be described in greater detail below, in some embodiments, the placement of the mapping catheter 14 and mapping of the phrenic nerve can be based at least in part on an anatomical cycle, such as a respiration or cardiac cycle.

Treatment Catheter

Once the phrenic nerve has been mapped, a treatment device, can be used to treat the patient. In some cases, the treatment device can form part of the mapping catheter, can be placed in the patient while the mapping catheter is still present (e.g., can fit within the lumen of the mapping catheter or vice versa), and/or can be a device that requires removal of the mapping catheter before insertion. One embodiment of a treatment device is the Artic Front Advance Cardiac Cryoablation Catheter, which is commercially available from Medtronic, and can be used to ablate the tissue.

Figure 3:
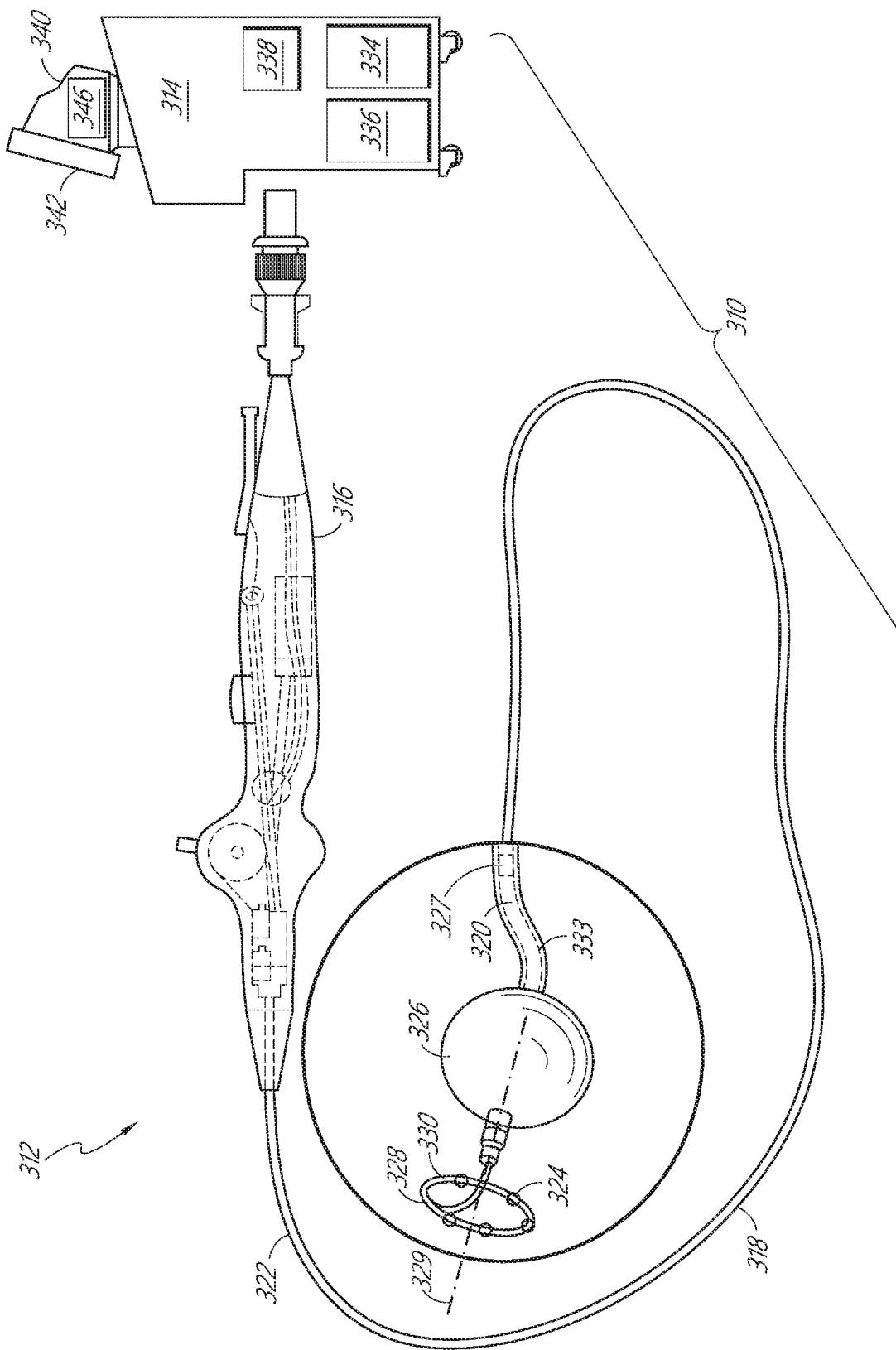
FIG. 3 is a diagram illustrating an embodiment of a cryoablation treatment system.

With reference to FIG. 3 below, the treatment device 312 can be a catheter with ablation, mapping, and/or audio sensing capabilities, and can have a longitudinal axis 329. The treatment device 312 can additionally include pacing capabilities. As a non-limiting example, the treatment device 312 can generally include a handle 316, an elongate body 318 having a distal portion 320 and a proximal portion 322, one or more recording electrodes 324 for detecting electrophysiological signals, one or more treatment elements 326 for ablating or thermally treating tissue, and/or one or more audio sensors 327 for recording sounds generated from the thoracic region of the patient's body (for example, audio signals from the heart and/or diaphragm).

In some embodiments, the one or more recoding electrodes 324 and pacing electrodes 328 can be included on an electrophysiology catheter 330. The electrophysiology catheter 330 can be can be used as a component of the treatment device 312 (as shown in FIG. 3) or as an independent device. Likewise, the one or more audio sensors 327 can be included on a separate device.

Figure 2:
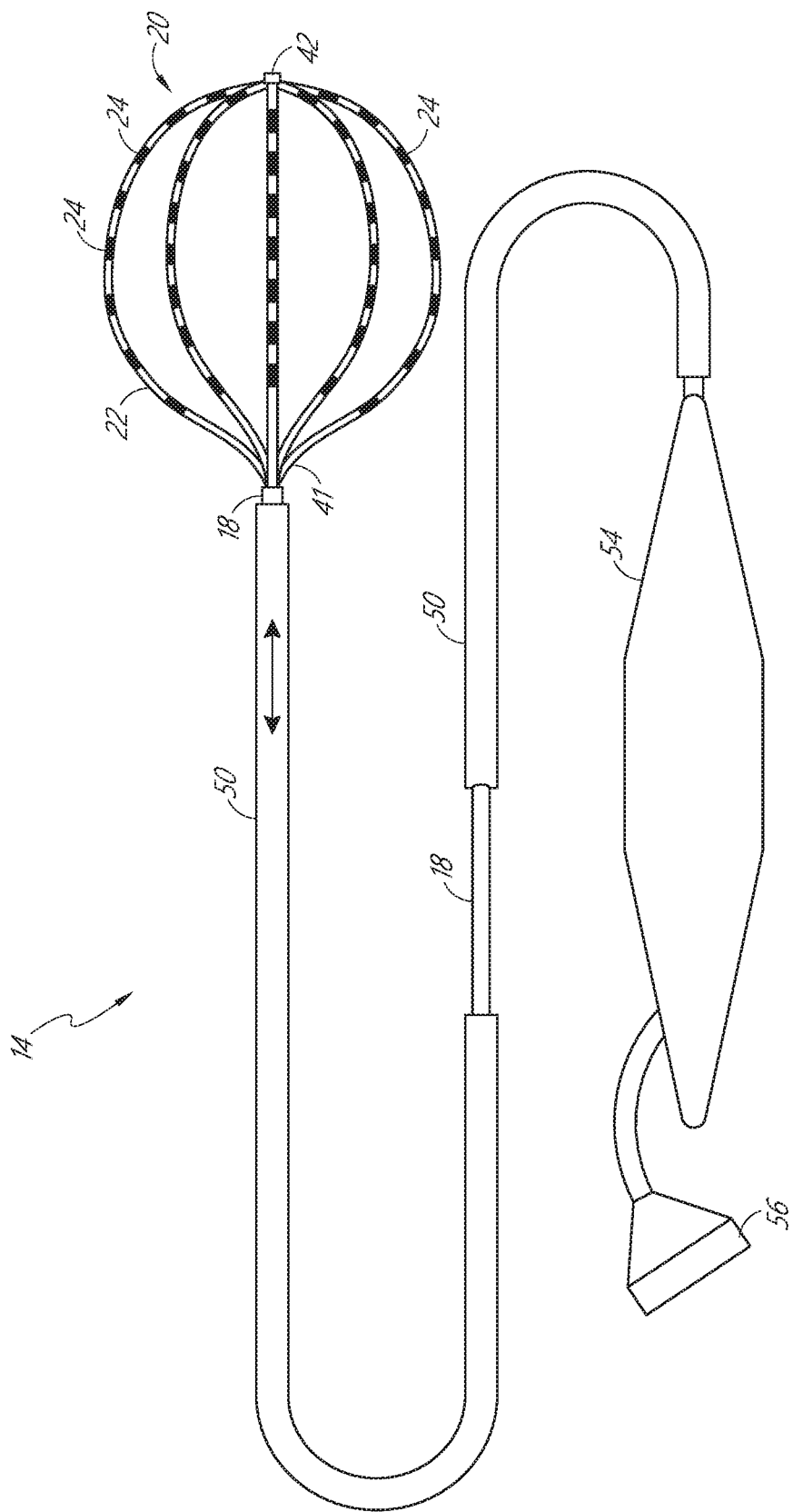
FIG. 2 is a diagram illustrating an embodiment of a mapping system.

The one or more treatment elements 326 can be coupled to or disposed on at least a portion of the distal portion 320 of the elongate body 318. For example, the one or more treatment elements 326 can include an expandable element (such as a cryoballoon as shown in FIG. 3, an expandable array of electrodes as shown in FIG. 2, an expandable conductive mesh, and the like). Alternatively, the one or more treatment elements 326 can be borne directly on the distal portion 320 of the elongate body 318 (for example, the treatment device 312 can be a fixed-diameter catheter such as a focal catheter).

The elongate body 318 of the treatment device 312 can include one or more lumens 333. If the treatment device 312 is a cryoablation catheter, for example, the elongate body 318 can include a main lumen, a fluid injection lumen in fluid communication with a coolant reservoir 334, and a fluid return lumen in fluid communication with a coolant return reservoir 336. In some embodiments, one or more other lumens can be disposed within the main lumen, can be disposed within the elongate body 318 along the longitudinal axis 329 parallel to the main lumen, and/or the main lumen can function as the fluid injection lumen or the fluid return lumen. If the treatment device 312 includes thermoelectric cooling elements or electrodes capable of transmitting RF (for example, the device shown in FIG. 2), ultrasound, microwave, HIFU, laser, hot balloon, electroporation energy, or the like, the elongate body 318 can include a lumen within which one or more wires are disposed, the wires being in electrical communication with one or more energy generators 338.

The console 314 can be in electrical and/or fluid communication with the treatment device 312 and can include one or more fluid (such as coolant or saline) reservoirs 334, fluid return reservoirs 336, energy generators 338 (for example, an RF or electroporation energy generator), and one or more computers 340 with displays 342, and can further include various other displays, screens, user input controls, keyboards, buttons, valves, conduits, connectors, power sources, and computers for adjusting and monitoring system 310 parameters. The computer 340 can be in electrical communication with the one or more treatment elements 326, the one or more recording electrodes 324, and/or the one or more audio sensors 327. Further, the computer 340 can include a processor 344 that includes one or more algorithms 346 executable to evaluate signals received from the one or more recording electrodes 324 and audio sensors 327 and to control, monitor, and/or suggest repositioning of the one or more treatment elements 326.

The treatment device 312 can be used in association with an electrophysiology catheter 330, with the treatment device 312 being used to ablate tissue and the electrophysiology catheter 330 being used to stimulate the phrenic nerve and, optionally, to record one or more electrophysiological signals from the heart. The electrophysiology catheter 330 can, for example, be slidably disposed within a lumen 333 of the device 312 such that the electrophysiology catheter 330 can be positioned within the patient's anatomy independently before advancing the treatment device 312 over the electrophysiology catheter 330 to a treatment location (as shown in FIG. 3). Alternatively, the electrophysiology catheter 330 can be usable independent of the device 312 (as shown in FIG. 3). The electrophysiology catheter 330 can be flexible (for example, capable of being deflectable into a hooped shape (as shown in FIG. 3) and/or into a shape that includes one or more curves or bends. Further, the electrophysiology catheter 330 can include one or more pacing electrodes 328 that can be used to stimulate the phrenic nerve by transmitting energy in frequencies around approximately 100 Hz or more, for example, in a series of pacing pulses.

Device Placement

Figure 4A:
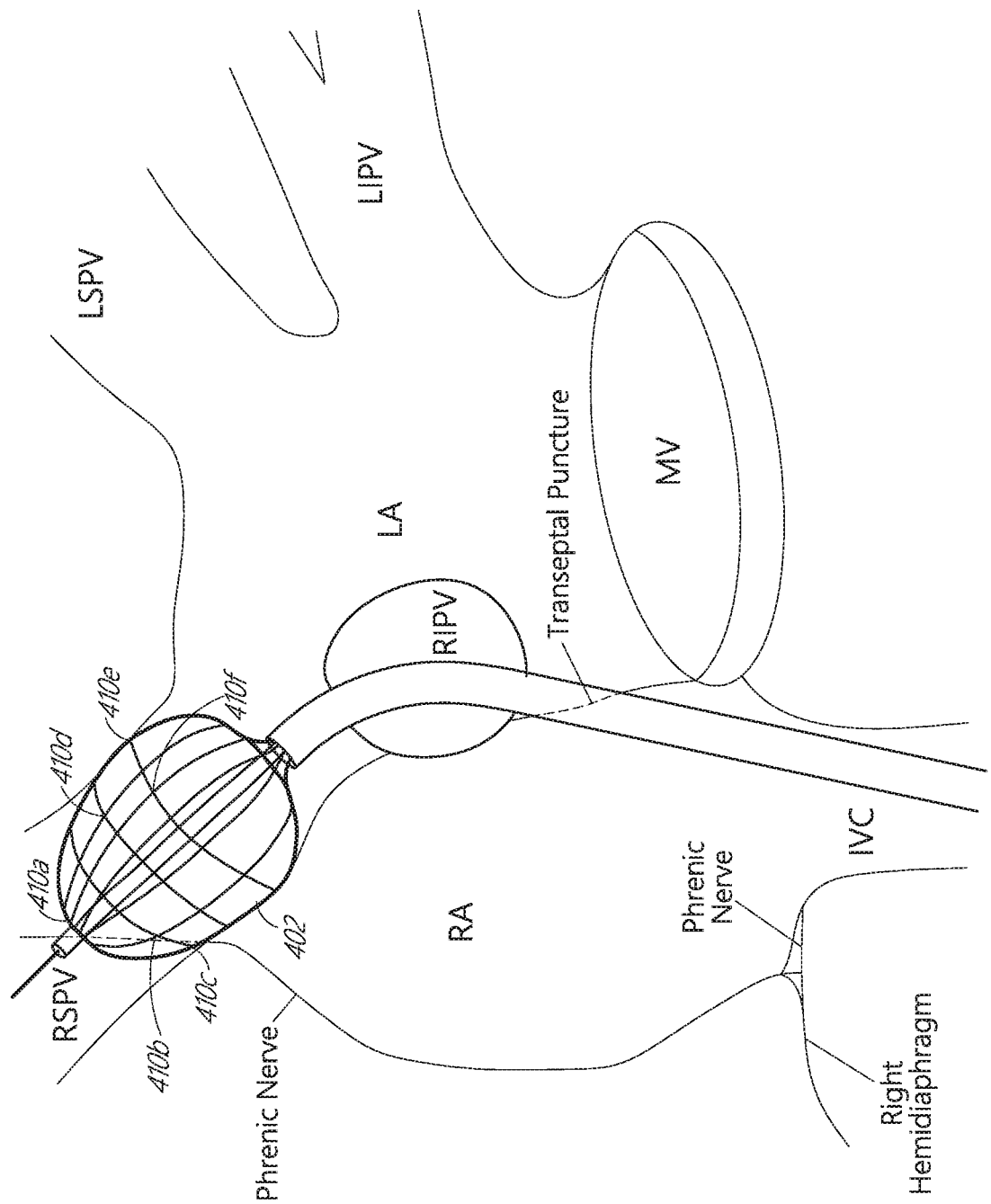
FIG. 4A is a diagram illustrating an embodiment of a mapping device of an intravenous catheter is positioned within the right superior pulmonary vein.

FIG. 4A is a diagram illustrative of an embodiment in which a mapping device 402 of an intravenous catheter is positioned within the right superior pulmonary vein (RSPV). FIGS. 4A, 4B, 6, and 9 further illustrate the relative locations of various anatomical features, including the right atrium (RA), left atrium (LA), phrenic nerve, right hemidiaphragm, right inferior pulmonary vein (RIPV), left superior pulmonary vein (LSPV), left inferior pulmonary vein (LIPV), inferior vena cava (IVC), and mitral valve (MV), with respect to various medical devices.

In the illustrated embodiments of FIGS. 4A, 4B, 6, and 9, the catheter has been moved intravenously to the heart and entered the left atrium via a transeptal puncture. In addition, in the illustrated embodiment of FIG. 4A, the mapping device 402 has been expanded to the circumference of the RSPV near the PV-LA junction.

The location of the mapping device 402 (and/or catheter) can be determined in a variety of ways, such as by performing fluoroscopy or a venogram, tracking the location of the mapping device 402, using a 3D mapping system, occlusive venography, ultrasound (intracardiac echo or transesophageal echo), contact force sensors (e.g., the difference in impedance when in contact with tissue vs. not in contact can be compared), fiber optics, etc. In some embodiments, the determined location of the mapping device 402 can be traced onto a live fluoroscopy image.

Once the mapping device 402 is positioned in the desired location, the mapping device 402 can be expanded until contact is made on all sides of the PV (e.g., a circumference or perimeter of the mapping device 402 is in contact with the PV). A variety of techniques can be used to determine whether there is adequate juxtaposition to the wall of the pulmonary vein/antrum, such as, but not limited to, venography, an occlusive balloon venogram, a self-expanding nitinol array, contact force sensors, direct visualization in the case of an array mounted to or in direct contact with a balloon (fiber optics), or with intracardiac echo, etc.

Furthermore, as described above, once the mapping device 402 is placed within the RSPV, one or more of the electrodes of the mapping device 402 can be activated to pace and map (or determine the location of) the phrenic nerve. In some embodiments, multiple electrodes are activated to identify the location of (and map) the phrenic nerve. In certain embodiments, the electrodes are activated to identify the location of as much of the phrenic nerve as possible (e.g., the portions of the phrenic nerve that can be paced by the electrodes of the mapping device 402). As discussed previously, activation of the electrodes closer to the phrenic nerve can result in a stronger, or more pronounced, diaphragmatic contraction (or other observable reaction). For example, in the illustrated embodiment, electrodes 410a, 410b, 410c can result in a stronger diaphragmatic contraction than the activation of electrodes 410d, 410e, 410f. One may detect very proximal phrenic nerve stimulation and mapping of the phrenic nerve may extend into the PV antrum/atrium. The mapping array can be positioned in the PV antrum/atrium to complete the evaluation of the full extent of the phrenic nerve stimulation including the most proximal region of the phrenic nerve.

Using the results of the activation of the electrodes, the portions of the phrenic nerve near the mapping device 402 (and targeted tissue region) can be located and the phrenic nerve can be mapped. For example, a display can display the determined location of the phrenic nerve, the location of the electrodes that paced the phrenic nerve, and/or the (relative) strength of the contraction (or other observed reaction) when the particular electrode is activated compared to other electrodes. In this way, a map of the phrenic nerve can be achieved. The determined location and/or mapping of the phrenic nerve can be used to treat the targeted tissue region.

Figure 4B:
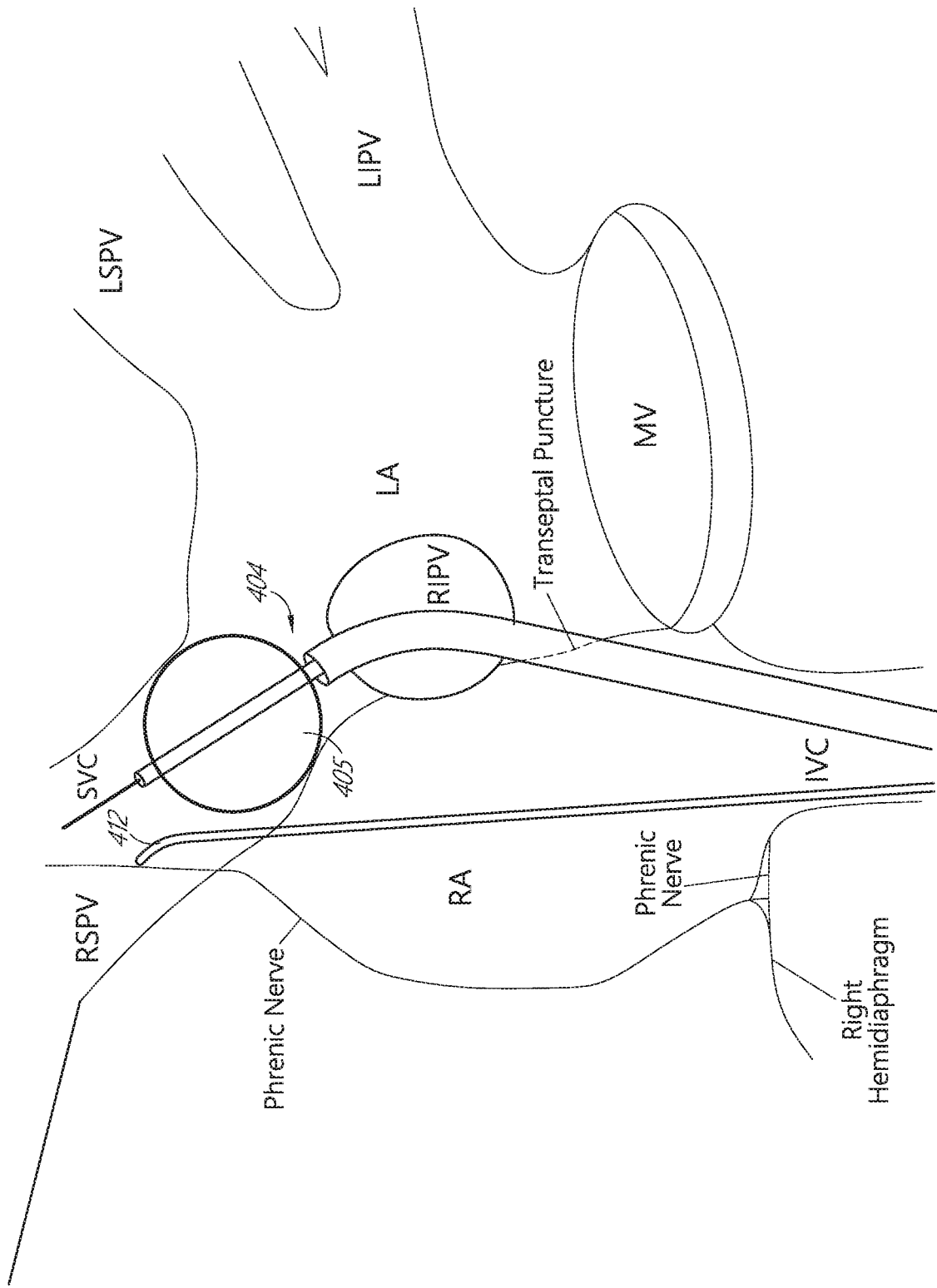
FIG. 4B is a diagram illustrating an embodiment of a treatment device positioned within the right superior pulmonary vein.

FIG. 4B is a diagram illustrative of an embodiment in which the mapping device 402 (and corresponding catheter) is replaced with a treatment device 404 having a treatment element 405, such as an inflatable balloon. For example, following the mapping of the phrenic nerve, the mapping device 402 (and corresponding catheter) can be removed and replaced with the treatment device 404.

In the illustrated embodiment, the treatment element 405 of the treatment device 404 is positioned and expanded within the RSPV at a similar location to the mapping device 402. Similar to the mapping device 402, in some embodiments, the treatment element 405 is expanded until contact is made on all sides of the PV (e.g., a circumference or perimeter of the treatment element 405 is in contact with the PV). Contact with the PV can be determined similar to the methods described above with respect to the mapping device 402.

In some embodiments, the treatment element 405 can be positioned based at least in part on the determined location of the phrenic nerve (or its mapping), or portions thereof. For example, a display can display the phrenic nerve mapping while also displaying the location of the treatment element 405.

In certain embodiments, the treatment element 405 can be positioned based at least in part on the determined location of an identified proximal portion of the phrenic nerve. In some embodiments, the identified proximal portion of the phrenic nerve is the portion of the phrenic nerve nearest to the PV-LA junction and/or the atrium.

Based at least in part on the proximity of the treatment element 405 to the determined location of the phrenic nerve (and/or the phrenic nerve mapping), a user can determine whether to proceed with treatment. For example, if the location of the treatment element 405 (and/or the portions thereof that are in contact with the PV) is distal to, or approximately equal to, the identified proximal portion of the phrenic nerve, the user can determine not to ablate because there can be a relatively high risk of PNI. If the treatment element 405 (and/or the portions thereof that are in contact with the PV) is proximal with respect to the identified proximal portion of the phrenic nerve, the user can determine whether there is a relatively intermediate or low risk of PNI (as a non-limiting example, <4 mm between the treatment element 405 and the phrenic nerve can indicate a relatively intermediate risk and >4 mm between the treatment element 405 and the phrenic nerve can indicate a relatively low risk, however, it will be understood that the level of risk can vary, for example, based on the treatment element 405 used, other factors, etc.).

In some embodiments, such as when there is a relatively intermediate risk, the treatment element 405 can be moved into the atrium, activated, and then pushed back into the PV. When activated, the circumference of the treatment element 405 can expand, which can reduce the distance in the vein to which the treatment element 405 can advance. For example, depending on the treatment device 404 used, the circumference of the treatment element 405 can expand from 26 mm to 28 mm. In this way, the physician can decrease the relative risk of PNI by increasing the distance between the phrenic nerve and the treatment element 405 during ablation as a larger diameter balloon will "wedge" at a more proximal location.

In the event the user determines to proceed with the treatment, the phrenic nerve can be monitored for potential injury during the treatment procedure. For example, the phrenic nerve can be paced (for example, by activating one or more electrodes of a catheter positioned in the superior vena cava (SVC) adjacent to the phrenic nerve and superior to the site of ablation in the pulmonary vein). If a reduction of the force of diaphragmatic contraction is detected (or other observable reaction changes) during ablation, the ablation procedure can be stopped. For example, the balloon can be forcibly deflated and a corresponding ice shell fractured with saline.

In the illustrated embodiment of FIG. 4B, a second catheter is shown that includes a pacing electrode 412 positioned near a portion of the phrenic nerve superior to the treatment element 405 in or near the SVC. The second catheter can be used to pace the phrenic nerve during operation of the treatment device 404 in order to detect phrenic nerve injury. For example, during treatment, the pacing electrode 412 can be activated to pace the phrenic nerve. If the diaphragmatic contractions weaken (or other observable reactions change) while the placement of the pacing electrode and its electrical output remain the same (or approximately the same), a potential phrenic nerve injury can be determined and the procedure stopped.

Complementary Devices

FIGS. 5A-5D are diagrams illustrating embodiments of a complementary mapping device 502 and treatment device 504 in different configurations and positions. In some embodiments, the complementary mapping device 502 and treatment device 504 can be implemented as part of a single catheter. In certain embodiments, the mapping device 502 and treatment device 504 can be implemented as separate, complementary catheters. For example, a mapping catheter can be sized to fit within the lumen of the treatment catheter or vice versa. In the illustrated embodiment, a mapping catheter is placed within a lumen 503 of a treatment catheter. In addition, in the illustrated embodiment, a lumen 507 of the mapping device 502 and a guidewire 516 are shown.

The mapping device 502 and treatment device 504 can be placed within an outer sheath 506 and can be independently operated. For example, the mapping device 502 can be independently, moved, collapsed, and/or expanded as desired. Similarly, the treatment device 504 can be independently moved, and its corresponding treatment element 505 can be independently collapsed, and/or expanded as desired. In the illustrated embodiments, a lever 508 is used to control the position and configuration of at least the mapping device 502.

The mapping device 502 can be similar to the mapping device 20 described above with reference to FIG. 2. For example, the mapping device 502 can include multiple independently activatable electrodes 510 that can be used to pace and/or map the phrenic nerve.

Portions of the mapping device 502, such as portions of the tines 512 that are more proximate to the treatment element 505 and/or outer sheath, can be coupled to a runner 514. In the illustrated embodiment, the runner 514 can move telescopically within the treatment catheter. However, it will be understood that the runner 514 can be implemented in a variety of ways. For example, the runner 514 can form an extension of the treatment device 504, etc.

In the illustrated embodiment, the lever 508 controls the runner 514, causing the runner 514 to advance or retract. As the runner 514 moves, the configuration of the mapping device 502 can change. For example, as the runner 514 advances away from the outer sheath 506, the mapping device 502 can move from a collapsed configuration to an expanded configuration and from an expanded configuration to a treatment configuration. However, it will be understood that fewer or more configurations can be used as desired. For example, in some embodiments, the mapping device 502 can have two configurations: collapsed and expanded, or can have more than three configurations.

In some embodiments, the collapsed configuration can be used to advance the mapping device 502 through the patient and outer sheath 506. In the expanded configuration, the mapping device 502 can be used to pace and/or map the phrenic nerve, and in the treatment configuration, the mapping device 502 can be used to provide space for the treatment element 505, pace the phrenic nerve during tissue ablation and/or provide a buffer between the treatment element 505 and the phrenic nerve. One can also determine if the underlying tissues have been frozen by the loss of local electrograms upon freezing of the tissues.

The treatment element 505 can be similar to the treatment element 326, described in greater detail above with reference to FIG. 3. However, although illustrated as a cryoballoon catheter in FIGS. 5A-5D, it will be understood that the treatment device 504 and treatment element 505 can be implemented using a variety of devices and technologies, including, but not limited to, RF, high-frequency ultrasound (HIFU), laser, and/or hot balloon.

FIG. 5A is a diagram illustrating an embodiment of the complementary mapping device 502 and the treatment device 504 when the mapping device 502 is collapsed and the treatment element 505 is expanded. Although not illustrated, when the mapping device 502 and treatment device 504 are inserted into the patient, both can be in a collapsed position to enable movement through the patient and the outer sheath. Once the devices 502, 504 are positioned, each one can be independently expanded/collapsed as desired.

FIG. 5B is a diagram illustrating an embodiment of the complementary mapping device 502 and treatment device 504 when the mapping device 502 and the treatment element 505 are expanded. In the illustrated embodiments, the control lever 506 is moved to alter the configuration of the mapping device 502. As illustrated, when the control lever 506 is moved from a first position to a second position, the runner 514 advances and the mapping device 502 changes from a collapsed configuration to an expanded configuration. As described in greater detail above, in some embodiments, when in the expanded configuration, the mapping device 502 can be used to pace and/or map the phrenic nerve.

FIG. 5C is a diagram illustrating an embodiment of the complementary mapping device 502 and treatment device 504 when the mapping device 502 is moved to a third, or treatment, configuration. In the illustrated embodiments, when the control lever 506 is moved to a third position, the runner 514 advances further and the mapping device 502 changes to the third configuration. In the illustrated embodiment, in the third configuration, the mapping device 502 is in an umbrella shape, however, it will be understood that in the third configuration, the mapping device 502 can be put in any shape and/or can be collapsed and withdrawn from the tissue site as desired.

FIG. 5D is a diagram illustrating an embodiment of the complementary mapping device 502 and treatment device 504 when the mapping device 502 is in the treatment configuration and the treatment element 505 is moved in closer proximity to the mapping device 502. The treatment element 505 can be moved more proximate to the mapping device 502 by using the control lever 506, a separate control lever and/or by advancing the treatment catheter as desired. In some embodiments, by positioning the mapping device 502 in the treatment configuration and advancing the treatment element 505, the mapping device 502 can be used to pace the phrenic nerve while the treatment element 505 ablates the target tissue. Furthermore, the mapping device 502 can be used as a buffer between the treatment element 505 and the phrenic nerve in order to reduce the likelihood of PNI. Flexible heaters can regionally warm the non-targeted tissues by resistive heating during balloon cryoablation to reduce the likelihood of PNI.

In the illustrated embodiments of FIGS. 5A-5D, the runner 514 and lever 506 are used to adjust the configuration of the mapping device 502. However, it will be understood that the configuration of the mapping device can be adjusted in a variety of ways as desired. For example, a button or cord can be used to adjust the configuration and/or move the mapping device 502 and/or treatment device 504.

Figure 6:
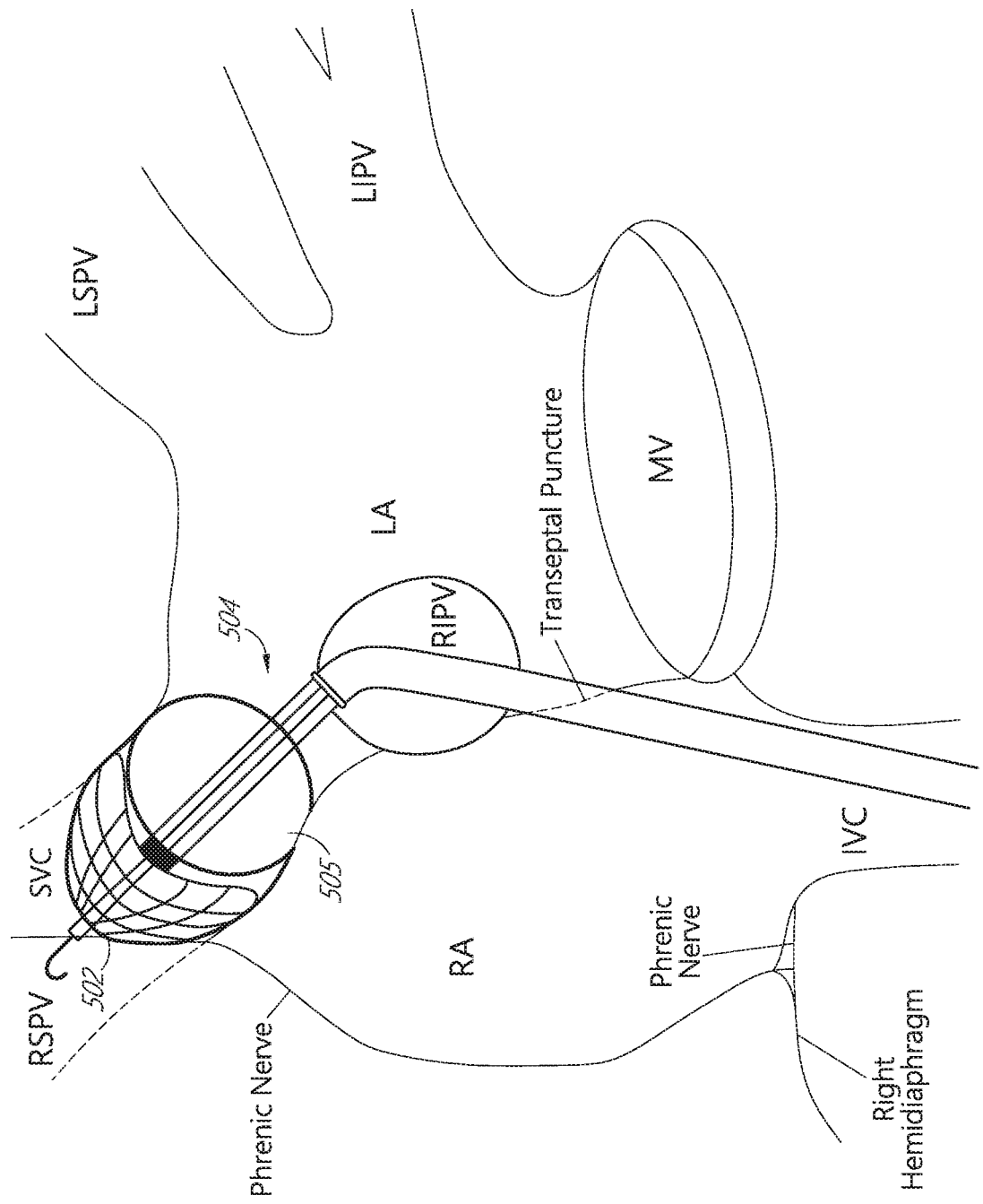
FIG. 6 is a diagram illustrative of an embodiment of a complementary mapping device and treatment device positioned within the right superior pulmonary vein.

FIG. 6 is a diagram illustrative of an embodiment in which the complementary mapping device 502 and treatment device 504 are positioned within the right superior pulmonary vein (RSPV). In the illustrated embodiment, the configuration of the complementary mapping device 502 and treatment device 504 are similar to the configuration shown in FIG. 5D. For example, FIG. 6 can represent an embodiment in which the phrenic nerve has been mapped using the mapping device 502 and a healthcare provider is ready to treat the targeted tissue with the treatment device 504. As described above, in such a configuration, the treatment element 505 can be used to treat the targeted tissue. In addition, the mapping device 502 can be used to pace the phrenic nerve during treatment (e.g., at a location superior to the location of treatment) and/or provide a buffer between the treatment element 505 and the phrenic nerve during treatment. Furthermore, the location and placement of the devices 502, 504 can be determined similar to the manner in which the location of the mapping device 402 and treatment device 404 are determined.

Anatomical Cycle

In some embodiments, the determined placement and/or use of a medical device, such as the mapping device 20/402/502 and/or the treatment device 312/404/504, can be based at least in part on an anatomical cycle, such as a respiration or cardiac cycle.

In some cases, during a procedure, anatomical cycles can cause portions of relevant tissue to move in a cyclical pattern with respect to the location of a medical device. For example, during the respiration cycle, the heart can move several centimeters depending on the tidal volume.

By taking into account movement due to the anatomical cycle in determining the location/use of a medical device, a user can increase the likelihood that two medical devices have been placed in the same location at different times, and reduce the likelihood of treating undesired tissue. For example, a user can increase the likelihood that the treatment element 326/405/505 has been placed in the same location that the mapping device 20/402/502 was when mapping the surrounding tissue (e.g., when mapping the phrenic nerve). In some cases, the amount of tissue movement due to an anatomical cycle can be reduced, such as by using jet ventilation in a non-paralyzed patient.

As a non-limiting example, at a particular portion of an exhalation cycle, such as at end exhalation, the location of the mapping device 20/402/502 can be determined. The location can be determined in a variety of ways, such as by performing fluoroscopy or a venogram, tracking the location of the mapping device 20/402/502 using a 3D mapping system, occlusive venography, ultrasound (intracardiac echo or transesophageal echo), contact force sensors (e.g., the difference in impedance when in contact with tissue vs. not in contact can be compared), fiber optics, etc. In some embodiments, the determined location of the mapping device 20/402/502 can be traced onto a live fluoroscopy image. The electrodes of the mapping device 20/402/502 can be paced and the location of the phrenic nerve determined. In addition, the location of some or all of the phrenic nerve, timed to end exhalation can be displayed on the live fluoroscopy image.

In some embodiments, once the mapping device 20/402/502 is moved or replaced with the treatment device 312/404/504, the location of the treatment device 312/404/504 can be determined. In certain embodiments, the location of the treatment device 312/404/504 and/or treatment element 326/405/505 can be determined, timed to end exhalation. The determined location can then be compared to the determined location of the phrenic nerve and/or the mapping device 20/402/502, and the user can determine whether to proceed with the procedure as described above.

Phrenic Nerve Injury Risk Determination Examples

Figure 7:
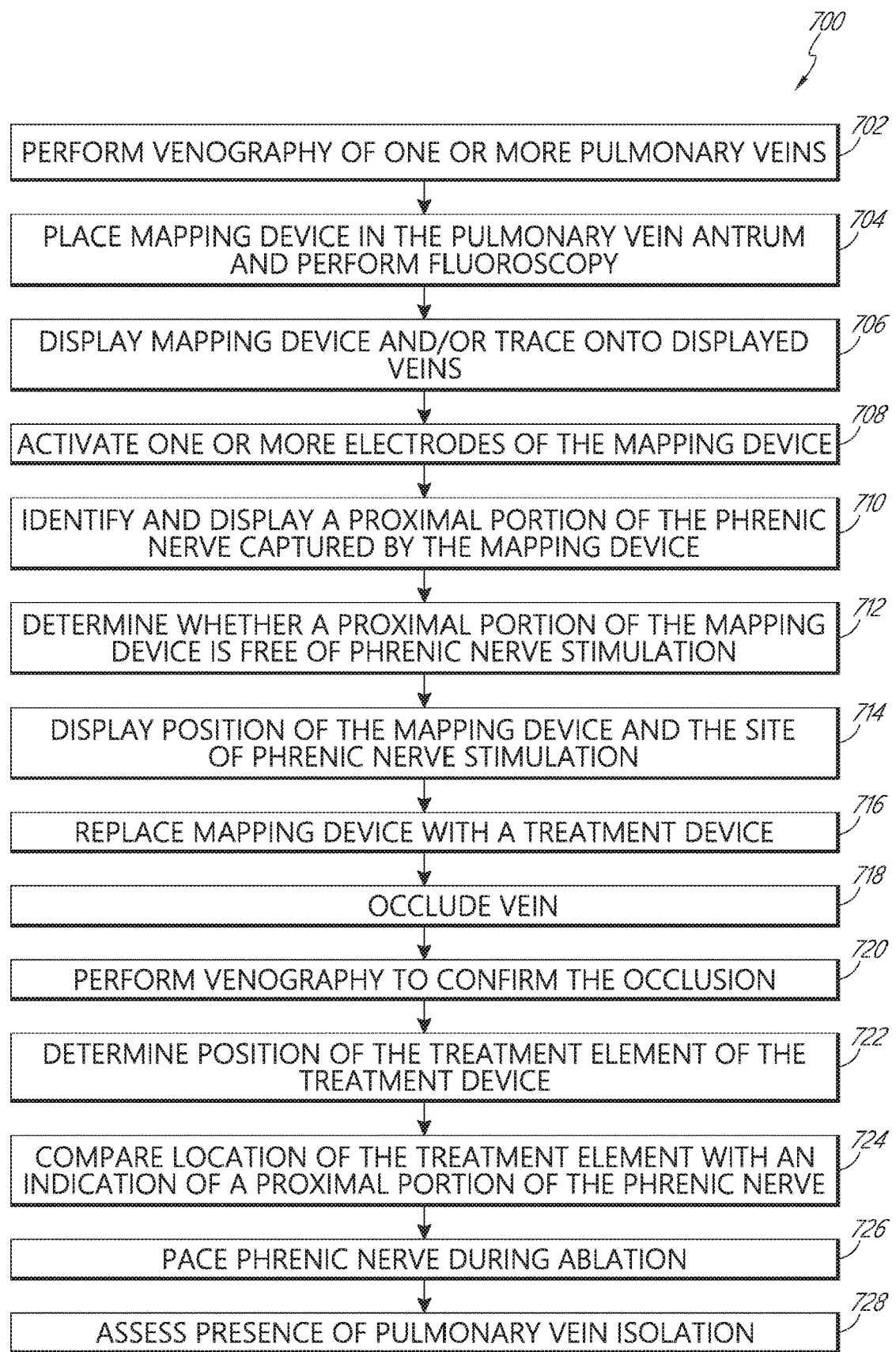
FIG. 7 is a flow diagram illustrating an embodiment of a routine for treating cardiac arrhythmia.

FIG. 7 is a flow diagram illustrating an embodiment of a routine 700 for treating cardiac arrhythmia.

At block 702, a venography is performed of one or more pulmonary veins of a patient. In some embodiments, the venography can be performed for the right-sided pulmonary veins and/or can be displayed in at least two orthogonal views. In certain embodiments, the venography can be timed to end exhalation. In some cases, the patient is spontaneously breathing (e.g., not paralyzed, not being assisted by the ventilator).

At block 702, the veins are displayed on a screen, such as a live fluoroscopy screen. In certain embodiments, the veins can be displayed timed to end exhalation and/or in at least two orthogonal views.

At block 704, a mapping device is placed in the pulmonary vein and/or pulmonary vein antrum and a fluoroscopy is performed to determine its location. In some embodiments, the fluoroscopy can be performed in the same view as those used in block 702 and/or can be timed to end exhalation.

At block 706, the mapping device is displayed and/or traced onto the displayed veins. In certain embodiments, the mapping device can be displayed timed to end exhalation.

At block 708, one or more electrodes of the mapping device are activated to determine the location of the phrenic nerve. As described in greater detail above, the activation of the electrodes can be used to determine the location of the phrenic nerve in the pulmonary vein and/or pulmonary vein antrum with respect to the mapping device. In some embodiments, the activation of the electrodes can be done at high output (e.g., 20 mA at 9 ms asynchronously).

At block 710, a proximal portion of the phrenic nerve captured by the mapping device is identified and displayed. In some embodiments, the proximal portion of the phrenic nerve can be displayed in at least two orthogonal views and/or timed to end exhalation.

At block 712, it is determined whether a proximal portion of the mapping device (proximal with respect to a central axis that is orthogonal to a longitudinal axis of the mapping device) is free of phrenic nerve stimulation. If not, the mapping device can be retracted until the proximal portion of the mapping device is free of phrenic nerve capture. In certain embodiments, the phrenic nerve is paced with high output. In some embodiments, if the mapping device is moved, blocks 708 and 710 can be repeated.

At block 714, the position of the mapping device and the sites of phrenic nerve stimulation are displayed on a display. In some embodiments, the position of the mapping device and the sites of phrenic nerve stimulation can be displayed on a 3D mapping system.

At block 716, the mapping device is replaced with a treatment device, such as a treatment device 312/404/504, and at block 718 a treatment element of the treatment device is inflated to achieve occlusion. In some embodiments, the treatment element can be inflated after positioning the treatment element at one of the right-sided veins.

At block 718, the vein is occluded, and at block 720 a venography is performed to confirm the occlusion. In certain embodiments, the venography can be performed through a distal port of the treatment device and/or can be timed to end exhalation.

At block 722, the position of the treatment element of the treatment device is determined relative to the most proximal site of phrenic nerve stimulation. In some embodiments, the position can be determined timed to end exhalation.

At block 724, the location of the treatment element is compared with an indication, such as a line or other graphic, of a most proximal portion of the phrenic nerve. If the treatment element overlaps the indication, the location is identified as high risk. If the treatment element is located within four millimeters of the indication, the location is identified as intermediate risk. If the treatment element is located greater than four millimeters of the indication, the location is identified as low risk. If the location is identified as high risk, the treatment element can be repositioned to an intermediate risk position or low risk position.

At block 726, the phrenic nerve is paced while ablating. During the ablation, if a reduction of the force of diaphragmatic contraction is detected by palpation, the position of the catheter in the SVC can be verified. If the location was identified as low risk and the catheter pacing the phrenic nerve has moved, excursion of the right hemidiaphragm can be verified using fluoroscopy.

If a weakening of the diaphragm is detected fluoroscopically, the treatment element can be forcibly deflated and the ice shell fractured with saline administered through the distal port. If the diaphragm is moving normally on fluoroscopy, the treatment element can be repositioned in the SVC to regain phrenic nerve capture and the ablation continued.

If the case was identified as intermediate risk and the diaphragmatic contraction weakens by palpation, the treatment element can be deflated and the ice shell fractured. Fluoroscopy can be performed to assess the motion of the right hemidiaphragm.

At block 728, the presence of pulmonary vein isolation (PVI) is assessed, and in certain cases, additional treatment provided. In some embodiments, PVI can be assessed by placing the mapping and/or treatment device at the pulmonary vein antrum and in the pulmonary vein, evaluating for the presence of local PV electrograms to determine the presence of entrance block, and pacing the pulmonary vein to determine the presence of exit block.

In response, if persistent PV conduction is detected, additional treatment can be provided. For example, in some cases, the earliest site of entrance conduction into the PV/PV antrum can be targeted with the treatment device. Additional sites can be treated based on additional assessments for PVI.

In addition, as part of the assessment, adenosine can be administered after PVI to determine the presence of dormant conduction. Following the administration of the adenosine, if PV conduction is detected, additional treatment can be provided. For example, the earliest site of entrance conduction into the PV can be targeted with the treatment device. In some cases, the presence of PVI can be repeatedly assessed until there is no evidence of dormant conduction.

It will be understood that the various steps described above can be performed in a variety of orders. Furthermore, some steps can be omitted. For example, in some embodiments, a 3D mapping system may not be used, etc. In certain embodiments, the anatomical cycle (e.g., end exhalation) can be ignored, such as, but not limited to, when a treatment device that includes mapping functionality is used. Furthermore, although described with respect to locating the phrenic nerve and the treatment of cardiac arrhythmia, it will be understood that routine 700 can be used to identify the location of non-targeted tissue near a tissue site in other locations of the body. For example, the mapping device can be placed at a tissue site other than the pulmonary vein, such as near the prostate, and electrodes activated to locate non-targeted tissue near the tissue site, such as nerves near the prostate or a proximal portion of non-targeted tissue near a tissue site. Once located, the mapping device can be replaced with a treatment device, and a treatment element of the treatment device inflated. The location of the treatment element can be compared with the determined location of the non-targeted tissue. Based on the comparison, it can be determined whether the location of the treatment element represents a relatively low risk, relatively intermediate risk, or relatively high risk. The treatment element can be moved or treatment can begin based on the determined risk level. During treatment, the non-targeted tissue can continue to be assessed, such as by stimulation. If an adverse reaction occurs, the treatment can be stopped.

Figure 8:
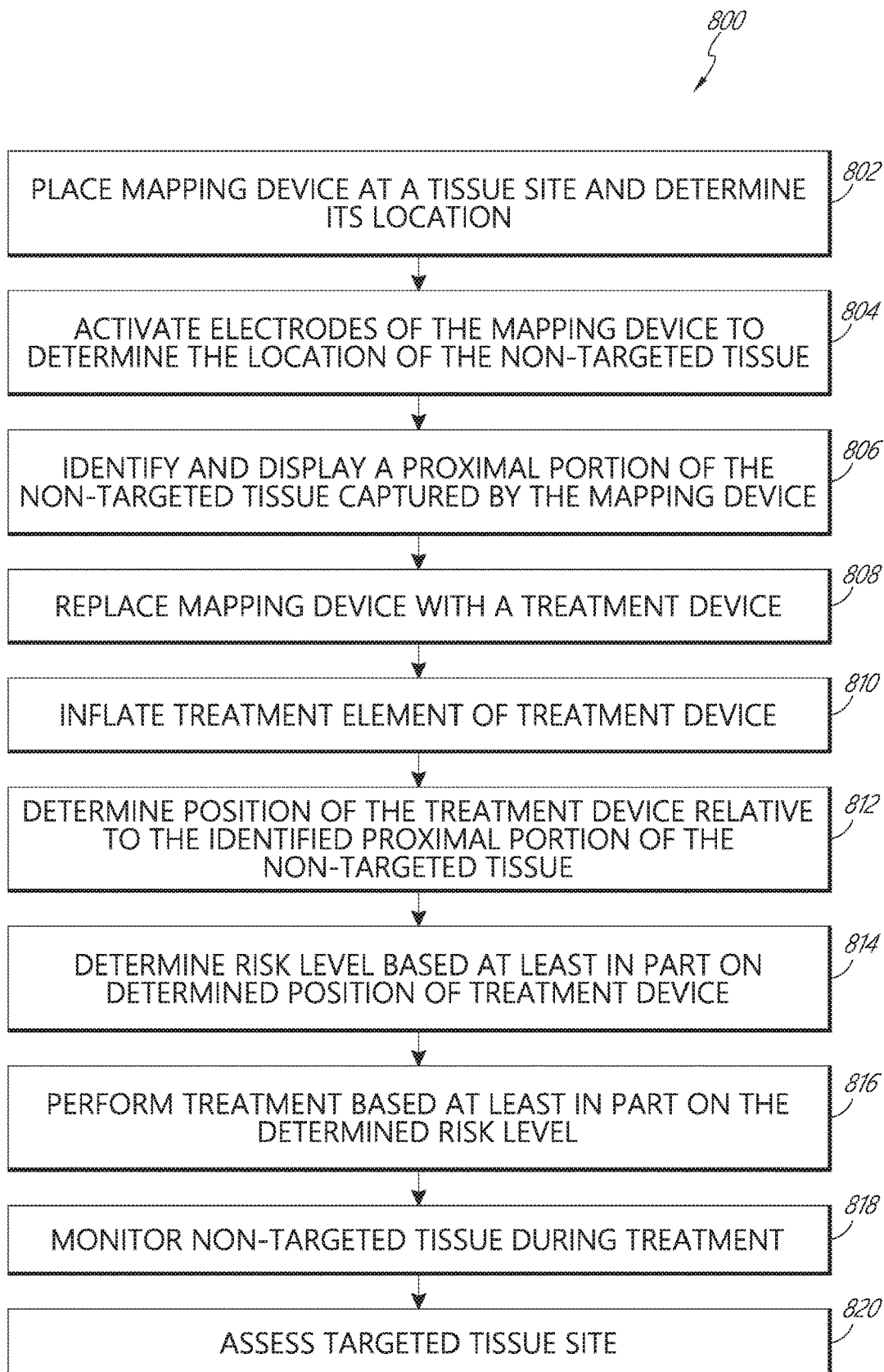
FIG. 8 is a flow diagrams illustrating an embodiment of a routine for treating a tissue site

FIG. 8 is a flow diagram illustrating an embodiment of a routine 800 for treating a tissue site. For example, routine 800 can be used to treat cardiac arrhythmia. Furthermore, it will be understood that any one or more of the blocks of routine 700 can be included with routine 800.

At block 802, a mapping device is placed at a tissue site and determine the location of the mapping device. In certain embodiments, the tissue site can be the pulmonary vein and/or pulmonary vein antrum. As described above, in some embodiments, a fluoroscopy is performed to determine the location. In some embodiments, its location can be determined timed to an anatomical cycle, such as end exhalation.

At block 804, one or more electrodes of the mapping device are activated to determine the location of non-targeted tissue with respect to the mapping device. In some cases, the non-targeted tissue can be the phrenic nerve. However, it will be understood that when used in other areas of the body, the one or more electrodes can be used to determine the location of other non-targeted tissue near a tissue site.

At block 806, a proximal portion of the non-targeted tissue captured by the mapping device is identified and displayed. In some embodiments, such as when treating cardiac arrhythmia, the proximal portion of the phrenic nerve can be identified. In certain cases, the determined location can be displayed in at least two orthogonal views and/or timed to a portion of the anatomical cycle, such as end exhalation.

At block 808, the mapping device is replaced with (or moved for) a treatment device.

At block 810, a treatment element of the treatment device is inflated for treatment. In certain embodiments, the treatment element is inflated to achieve occlusion of a vein.

Once it is determined that the treatment element is inflated to a satisfactory level, such as occlusion of the vein, at block 812 the position of the treatment element is determined relative to the identified proximal portion of the non-targeted tissue, such as the phrenic nerve. In some embodiments, the position of the treatment element is determined timed to a portion of the anatomical cycle, such as end exhalation.

At block 814, a risk level is determined based at least in part on determined position of the treatment element relative to the identified proximal portion of the non-targeted tissue.

At block 816, the treatment is performed based at least in part on the determined risk level. As described in greater detail above with reference to FIG. 7, in some embodiments, if the risk level is determined to be high, the treatment element can be moved.

At block 818, the non-targeted tissue is monitored during treatment. For example, the non-targeted tissue can be monitored by electrical stimulation or other methods. If an adverse reaction is detected, the treatment element can be moved or the treatment stopped.

In embodiments in which the phrenic nerve is paced, during the ablation, if a reduction of the force of diaphragmatic contraction is detected by palpation, the position of the catheter in the SVC can be verified. If the location was identified as low risk and the catheter pacing the phrenic nerve has moved, the fluoroscopy can be repositioned. If a weakening of the diaphragm is detected fluoroscopically, the treatment element can be forcibly deflated and the ice shell fractured with saline administered through the distal port. If the diaphragm is moving normally on fluoroscopy, the treatment element can be repositioned in the SVC to regain phrenic nerve capture and the ablation continued. If the case was identified as intermediate risk and the diaphragmatic contraction weakens by palpation, the treatment element can be deflated and the ice shell fractured. Fluoroscopy can be performed to assess the motion of the right hemidiaphragm.

At block 820, the targeted tissue site is assessed, and in certain cases, additional treatment provided. In some embodiment, once an initial treatment is completed, the tissue at the targeted tissue site can be examined to determine whether additional treatment is to be provided. For example, electrical signals near the targeted tissue site can be monitored.

With respect to embodiments in which cardiac arrhythmia is being treated, the presence of PVI can be assessed. In some embodiments, PVI can be assessed by placing the mapping and/or treatment device at the pulmonary vein antrum and in the pulmonary vein, evaluating for the presence of local PV electrograms to determine the presence of entrance block, and pacing the pulmonary vein to determine the presence of exit block. In response, if persistent PV conduction is detected, additional treatment can be provided. For example, in some cases, the earliest site of entrance conduction into the PV/PV antrum can be targeted with the treatment device. Additional sites can be treated based on additional assessments for PVI. In addition, as part of the assessment of PVI, adenosine can be administered after PVI to determine the presence of dormant conduction. Following the administration of the adenosine, if PV conduction is detected, additional treatment can be provided. For example, the earliest site of entrance conduction into the PV can be targeted with the treatment device. In some cases, the presence of PVI can be repeatedly assessed until there is no evidence of dormant conduction.

Fewer or more steps can be included as desired. For example, if the risk level is high, the treatment device can be moved. If the risk level is intermediate, the treatment device can be withdrawn from the tissue site, activated, and re-inserted into tissue site as described above. Furthermore, with respect to treating cardiac arrhythmia, during ablation, the phrenic nerve can be monitored and action taken, as described in greater detail above with reference to FIG. 7. For example, in some cases, if weakening diaphragmatic contractions are detected, the treatment element can be deflated and an ice shell broken.

In addition, although specific embodiments are described with respect to identifying the location of the phrenic nerve during treatment of cardiac arrhythmia, it will be understood that routine 800 can be used to identify non-targeted tissue near targeted tissue sites during treatment of other areas of the body. For example, the greater and lesser cavernous nerves (non-targeted tissues) pass nearby the prostate gland and can be injured during prostate surgery causing erectile dysfunction. By identifying the location of the nerves prior to treatment, the likelihood of injury can be reduced.

Segmented Treatment Element

Figure 10B:
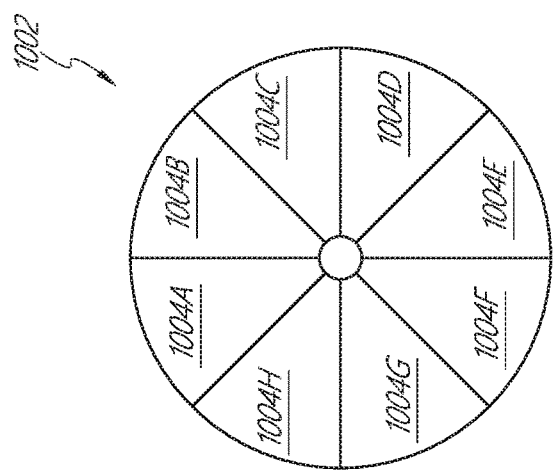
FIGS. 9, 10A and 10B are diagrams illustrating embodiments of treatment elements that include multiple segments.
Figure 10A:
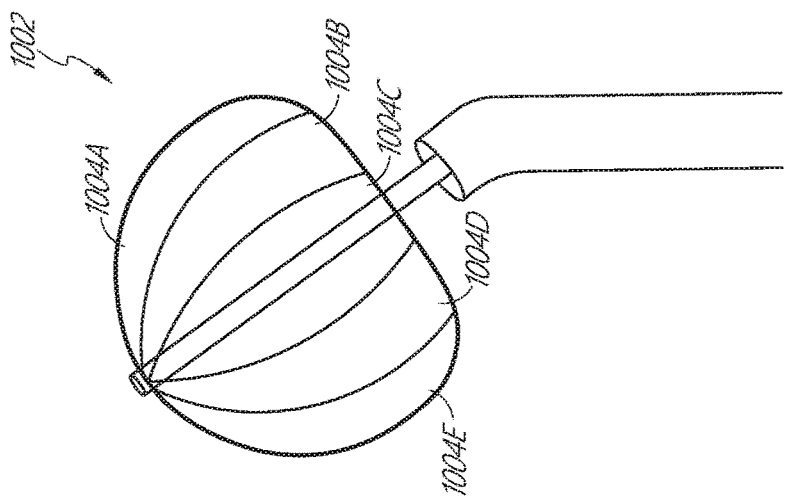
Figure 9:
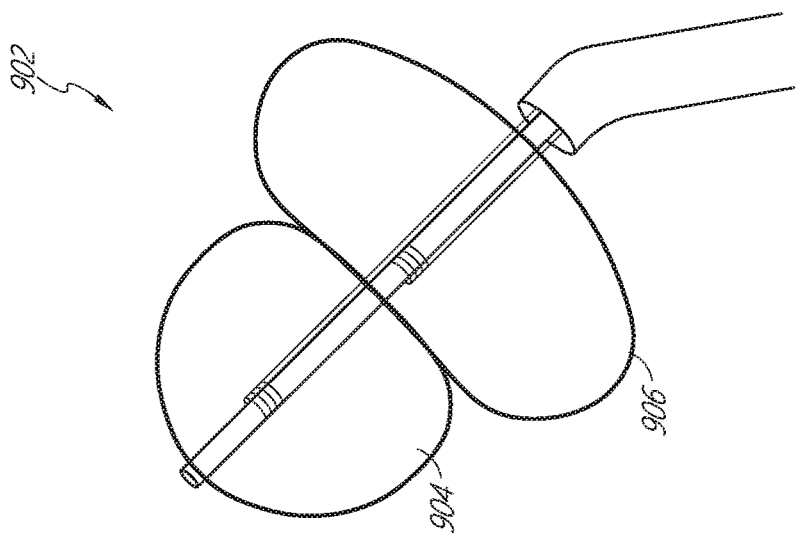

FIGS. 9, 10A and 10B are diagrams illustrating embodiments of treatment elements 902, 1002 of treatment devices that include multiple segments, which can also be referred to as cells or compartments. Each segment can be formed by a separate inflatable device, such as a balloon, and/or encompass a distinct location and volume with respect to the other segments. Furthermore, each segment can include walls that separate it from the other segments.

In the illustrated embodiment of FIG. 9, the treatment element 902 includes two segments: a distal segment 904 and a proximal segment 906. Further, in the illustrated embodiment of FIG. 9, the distal segment 904 is smaller than the proximal segment 906. However, it will be understood that the segments can be the same size or the proximal segment 906 can be smaller than the distal segment 904.

In the illustrated embodiment of FIGS. 10A and 10B, the treatment element 1002 includes eight segments 1004A, 1004B, 1004C, 1004D, 1004E, 1004F, 1004G, 1004H that extend from a distal portion central lumen to a more proximal portion of the central lumen forming approximately equal partitions of the distal end of the treatment device corresponding to the treatment element, and which can also be referred to as wedge segments. It will be understood that the embodiments shown in FIGS. 9, 10A, and 10B can be combined as desired and/or fewer or more segments can be used as desired. For example, the distal segment 904 and/or the proximal segment 906 can include multiple wedge segments and/or the treatment element 902 can include fewer or more segments, such as a central segment, etc. Similarly, the treatment element 1002 can include proximal and distal segments as desired and can include fewer or more wedge segments.

In certain embodiments, the cells can be independently controlled. For example, in some embodiments, each segment (or a subset of the total number of segments) can be independently and variably expanded and/or contracted. Furthermore, each segment (or a subset of the segments) can be independently heated or cooled.

In some cases, segments determined to be in close proximity to the phrenic nerve and/or esophagus can be converted to warming segments. For example, the distal segment 904 can be used for cryoablation during ablation of left sided PVs, and the proximal segment 906 can be a warming segment if the esophagus satisfies a distance threshold or temperature threshold, or is too close or became too cold during ablation of the left sided pulmonary veins.

Similarly, in cases where the distal segment 904 is determined to be too close to the phrenic nerve (for example, by pacing the phrenic nerve) or other tissue that is not to be treated, the proximal segment 906 can be used to cryo-ablate tissue and the distal segment 904 can be deflated and not used to cryoablate, inflated but not used to cryoablate, or inflated and used as a warming segment.

The segments can be made of a compliant material, such as polyurethane, polyester, composite material, laminate, or other material that allows for variable sizing to enable contact with the surrounding tissue, such as a pulmonary vein antrum, and to seal leaks between the surrounding tissue and the treatment element 902, 1002. The size of the segments can be adjusted by variably pressurizing during use, such as during cryoablation or warm high pressure mapping. As discussed in greater detail below, in certain cases, contact force sensors and flow sensors can be used to guide the appropriate size. If phrenic nerve location (or other tissue near a target site, but that is not to be treated) is a concern, high pressure warm mapping can be performed with to seal the tissue without risking injury to the nerve. In this way, the operator can test the occlusion of a vein, or other tissue, without risking injury to the surrounding tissue.

With respect to the treatment elements in FIGS. 10A and 10B, in some cases, if one or more of the segments 1004A, 1004B, 1004C, 1004D, 1004E, 1004F, 1004G, 1004H are determined to be too close to tissue that is not to be treated, the one or more segments 1004A, 1004B, 1004C, 1004D, 1004E, 1004F, 1004G, 1004H can be deflated, inflated without injecting high pressure refrigerant such as N2O to cryoablate, or used as warming segments either by applying a warming agent or leaving the segment empty of a solution.

Treatment Device with Sensors/Electrodes

Figure 11:
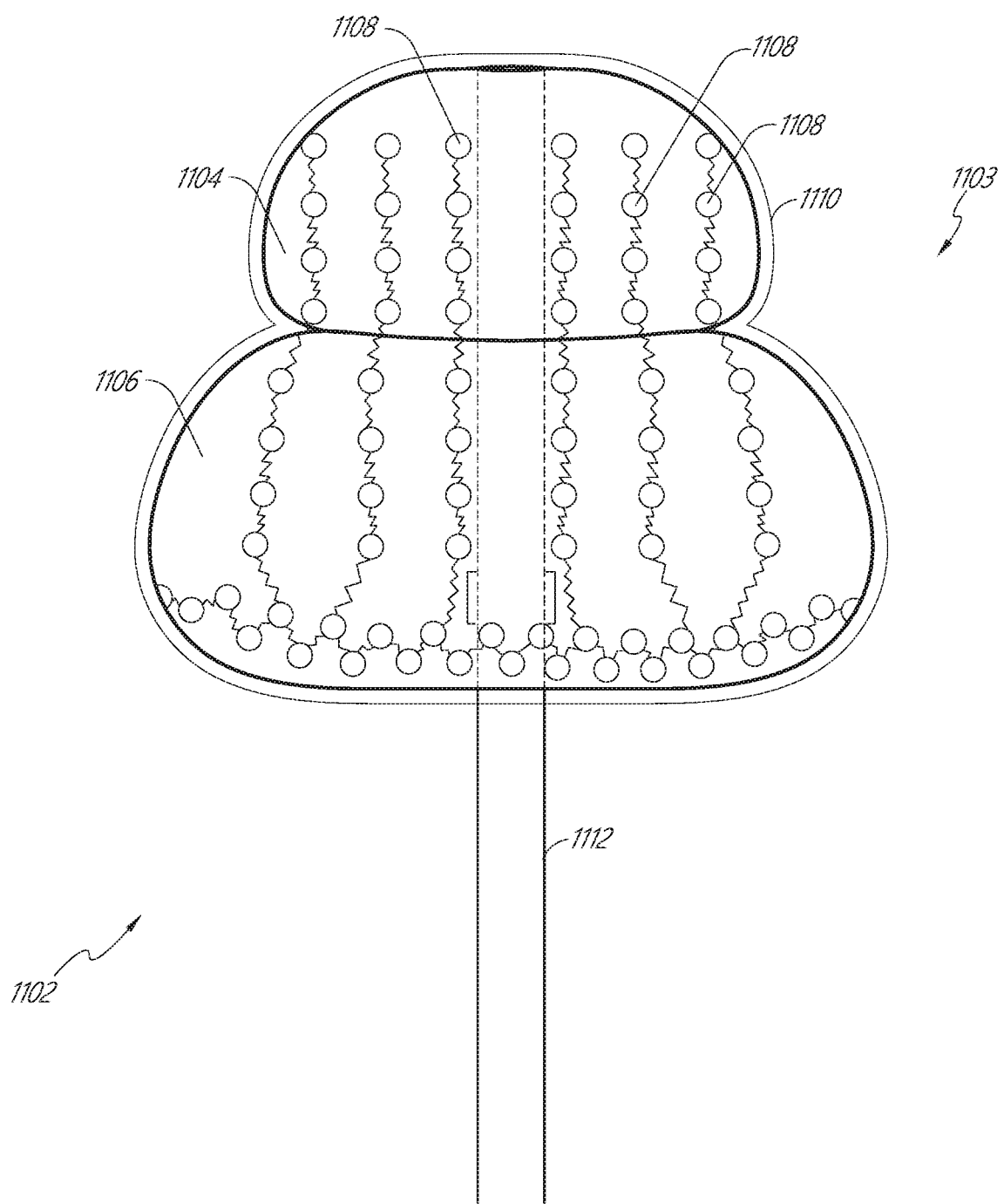
FIGS. 11 and 12 are diagrams illustrating embodiments of a treatment device that includes one or more sensor/electrodes.
Figure 12:
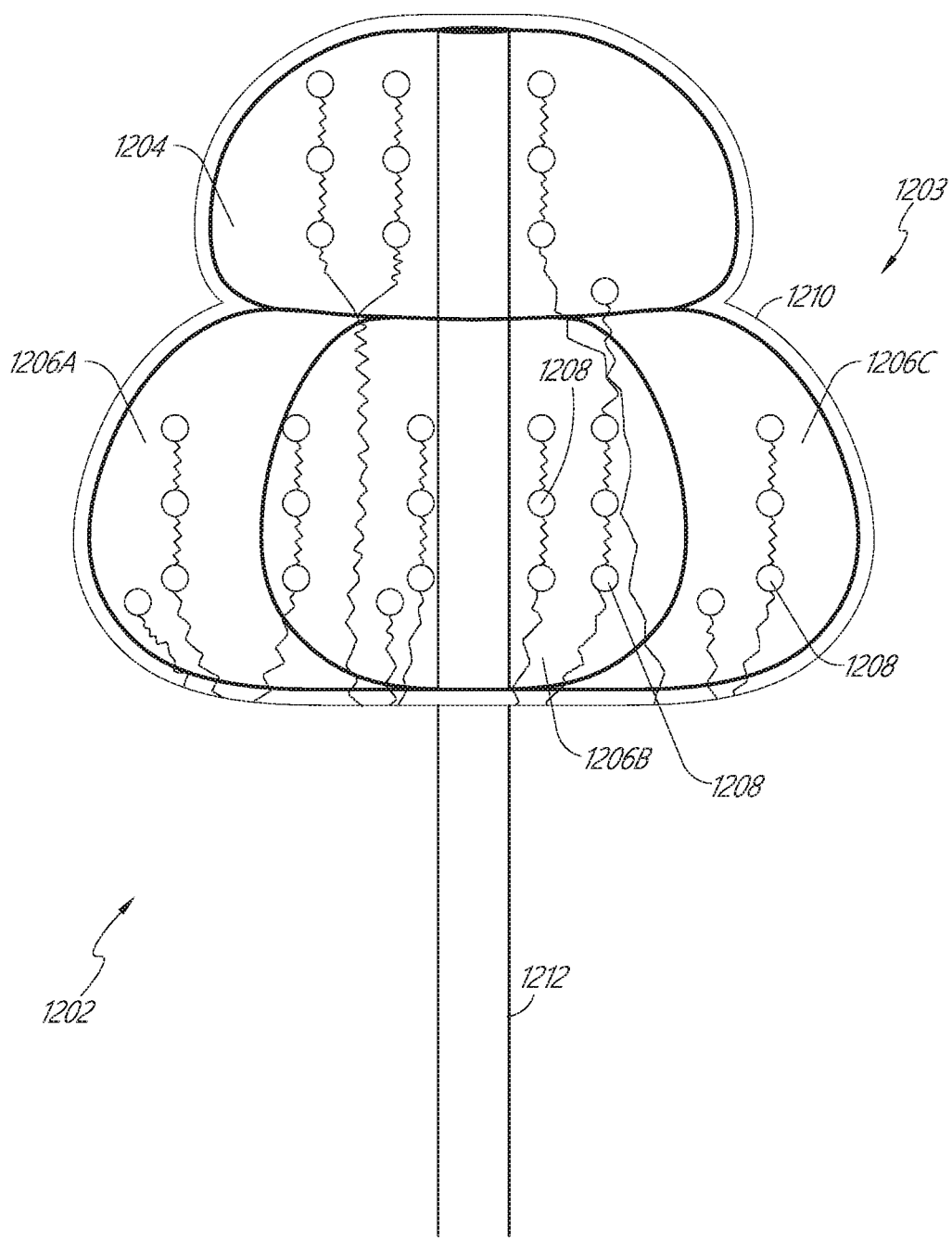

FIGS. 11 and 12 are diagrams illustrating embodiments of treatment devices 1102, 1202 that include one or more sensor/electrodes and can be used to pace and/or map the phrenic nerve and/or treat the targeted tissue region. Devices that can be used for mapping and treating a target location, such as treatment devices 1102, 1202, 1302 can also be referred to as an integrated device and/or an integrated treatment device. In some embodiments, when using the treatment devices 1102, 1202, the anatomical cycle can be ignored because the mapping and treatment devices described above are combined; provided however that the combined treatment devices are in direct contact with the targeted tissue during an anatomic cycle (non-limiting example: a combined treatment device positioned in PV antrum during an occlusive venogram. Furthermore, once the treatment device is inflated within the PV, the device can move with the tissue during the anatomical cycle. In some embodiments, the lumen of the treatment device 1102, 1202 can be flush with the distal end of the treatment device 1102, 1202, thereby allowing the treatment device to be used without a guide wire.

As described in greater detail above with reference to FIGS. 10A, 10B, and 10C, and as further illustrated in FIGS. 11 and 12, in some embodiments, the treatment device can include two or more segments, such as a distal and proximal segment. In certain embodiments, mapping electrodes can be included on the surface of the treatment device, thereby allowing accurate real time assessment of the location of the phrenic nerve.

In the illustrated embodiment of FIG. 11, a distal portion of treatment device 1102 is shown including central lumen 1112 and a treatment element 1103 that includes a distal segment 1104, a proximal segment 1106, a plurality of electrodes/sensors 1108. In the illustrated embodiment of FIG. 12, a distal portion of treatment device 1202 is shown including a central lumen 1212 and a treatment element 1203 that includes a distal segment 1204, four proximal segments configured as wedge segments 1206A, 1206B, 1206C, 1206D (not shown), and a plurality of electrode/sensors 1208. It will be understood that fewer or more compartments can be used as desired and that each of the segments can be independently controlled. Furthermore, each segment can be capable of cryoablation, cold mapping (low pressure), warm mapping (low pressure), warm fully inflated (high pressure), etc. It will be understood that warm mapping can include a solution at ambient temperature or a solution that is not cooled.

In some embodiments, the various segments of the treatment elements 1103, 1203 can be enclosed by an outer casing 1110, 1210, which can be formed of a compliant material, such as polyurethane with a vacuum between it and each of the interior segments to ensure safety in the event of a rupture of any of the segments 1104, 1204, 1106, 1206A-1306D. In some cases, the electrodes/sensors 1108, 1208 can be on the exterior of the outer casing 1110, 1210. In some embodiments, the sensors/electrodes 1108, 1208 can be integrated into the outer casing 1110, 1210.

As further illustrated in FIGS. 11 and 12, the treatment device 1102, 1202 can include a series of sensing, pacing, mapping, ablation electrodes, contact force sensors, and/or flow sensors (collectively electrodes/sensor 1108, 1208) designed to characterize tissue, such as the pulmonary vein and surrounding tissues in the vein, including the phrenic nerve. For example, the electrodes/sensors 1108, 1208 can be used to detect contact of the treatment element 1103, 1203 to the antrum of the pulmonary vein or the pulmonary vein itself, locate, any flow of blood around the treatment device, obtain pulmonary venous electrograms, locate/map/pace the phrenic nerve, and/or determine the temperature of the tissue adjacent to the phrenic nerve, esophagus, and/or the remainder of the antrum/pulmonary vein itself. As such, in certain embodiments, the treatment device 1102, 1202 can be utilized as a 3D mapping catheter able to collect 3D volume and activation times.

In some embodiments, the pacing electrodes can be used to stimulate surrounding tissue, such as a phrenic nerve. Based on the stimulation, the treatment device 1102, 1202 can generate a map of the surrounding tissue.

The sensing electrodes can be used to detect electrical or other activity. For example, the sensing electrodes can identify electrical activity before and/or after the procedure. Before the procedure, the data from the sensing electrodes can be used to identify a location of tissue that is to be ablated. Following the procedure, the data from the sensing electrodes can be used to determine whether the procedure was successful.

The contact force sensors can be used to detect contact of the treatment element 1103, 1203 to surrounding tissue and/or whether the tissue is properly occluded. The flow sensors can be used to detect any flow of blood or other substance around the treatment device and/or to determine whether the tissue is properly occluded.

Ablation electrodes can be used to isolate the pulmonary vein, in the event that the proximal segment of the treatment element 1103, 1203 satisfies a distance threshold with respect to the phrenic nerve (for example, is too close to the phrenic nerve and/or cryoablation risks phrenic nerve injury). Additionally, the ablation electrode can be used for radiofrequency touchup to improve the ablation of certain tissue and/or increase likelihood of a successful procedure. In certain cases, the ablation electrodes can be configured in a ring. In some embodiments, the inclusion of ablation electrodes with the treatment device 1102, 1202 can replace the use a separate radiofrequency catheter.

The temperature sensors can be used to monitor the temperature of tissue, before, after, or during ablation. Based on the temperature sensor data, the treatment element 1103, 1203 can be moved and/or the procedure halted. In some embodiments, the temperature sensors can be positioned on the treatment element 1103, 1203 adjacent to mapping electrodes and can demonstrate the temperature of the various regions of the treatment element 1103, 1203. The temperature of electrodes/sensors 1108, 1208 near sites of phrenic nerve (or other tissue) stimulation can be used to assess the risk of injury and can help in the prevention of injury in intermediate risk cases. If the local temperature of electrodes/sensors 1108, 1208 near the phrenic nerve (or other relevant tissue) satisfy a temperature threshold and/or are too cold, cryoablation can be stopped prior to injury of the nerve.

The treatment device 1102, 1202 can include additional sensors/electrodes as desired. For example, the treatment device 1102, 1202 can include optical elements to visualize the effects of ablation on the tissue, e.g., looking for gaps in the ablation lines or rings.

In certain cases, the treatment device 1102, 1202 can include an ultrasound transducer that can be used to obtain geometry, determine if a leak is occurring (with color flow), determine the optimal size to inflate the treatment device 1102, 1202 to obtain contact with the antrum of the pulmonary veins, etc. In some cases, the ultrasound transducer to construct 3D geometry for accurate navigation of the treatment device 1102, 1202 without the use of fluoroscopy. Color flow can help determine the sizing of the treatment device 1102, 1202 to ensure occlusion even in cases of left common ostium.

In addition, in some cases, an esophageal temperature probe can be positioned close to the treatment device 1102, 1202, and in some cases, as close as possible. The pairing of the esophageal probe, with the treatment device 1102, 1202 can improve the ability to identify the location of the segments nearest the esophagus. The signals can be sent over to any physiologic recording system or 3D mapping system for viewing. In some cases, if the treatment device 1102, 1202 is moved, rotated, or otherwise manipulated, the tissue can be remapped.

The electrodes/sensors 1108, 1208 for each segment of the treatment elements 1103, 1203 can be paired with a return electrode/sensor specific to the segment, such that pacing or sensing on that wedge segment can result in the completion of the circuit and enable the treatment device 1102, 1202 to determine which segment is being evaluated on the console. For example, a return electrode can be paired with the distal segment 1204, such that pacing any electrode on the distal segment 1204 causes the completion of a circuit that enables the treatment device 1102, 1202 to recognize the distal segment 1204. If the electrode being paced captures the phrenic nerve, a press of a touch screen can identify the segment or sub-segment. In some cases, the screen can turn the corresponding segment red, or otherwise highlight the segment that is being paced. Once selected, the corresponding segment can be configured for a warm mode, either low or high pressure, or a cryoablation mode.

In some embodiments, when in a mapping mode, all segments of the treatment element 1103, 1203 can be inflated to map the tissue. The tissue can be characterized using the electrodes/sensors 1108, 1208. In some cases, the distal segment 1104, 1204 can be used to keep a firm position in the vein while the phrenic nerve is being pacing using the electrodes/sensors 1108, 1208.

In some embodiments, the segments of the treatment element 1103, 1203 that risk damaging tissue surrounding a target site, such as the phrenic nerve or esophagus, can be can be deflated and/or used as warming segments, whether at high pressure or low pressure. In addition, the temperature of the tissue adjacent to the target site can be monitored using the electrodes/sensors 1108, 1208 during the procedure.

Based on the data collected during the mapping mode, the treatment device 1102, 1202 can provide treatment (e.g., cryoablation, etc.) from any of the proximal 1106, 1206A-1306D, and/or distal segments 1104, 1204. If the phrenic nerve (or other tissue near a target site) is in jeopardy of being damaged and/or paralyzed by the distal segment 1104, 1204, the distal segment 1104, 1204 can be converted to a warming balloon, inflated without cryoablating, and/or deflated. As such, the treatment device 1102, 1202 can protect the phrenic nerve from cryoablation and also assess the function of the phrenic nerve by pacing the nerve using the electrodes/sensors 1108, 1208 that are positioned on the treatment element 1103, 1203.

In some embodiments, as described in greater detail above, the distal segment 1104, 1204 can remain cold mapping for cryoablation during ablation of left sided PVs, and the proximal segments 1106, 1206A-1306D can be used as warming segments if the esophagus satisfies a distance threshold or temperature threshold or becomes too cold during ablation of the left sided pulmonary veins.

As yet another example, the proximal segment(s) 1106, 1206A-1306D can be used to isolate the pulmonary vein. Pulmonary venograms can be assessed during the freeze to determine time to effect thereby reducing unnecessary additional cryoablation. In some embodiments, if it is determined that the mapped tissue is clear of any phrenic nerve activation and satisfies a threshold distance from the esophagus, all segments of the treatment element 1103, 1203 can be used to ablate.

Furthermore, in some cases, the treatment device 1102, 1202 can be used for a roof line or posterior wall isolation. The treatment device 1102, 1202 can assess for bidirectional block across the pulmonary vein antrum (pulmonary vein isolation), block across the roof of the left atrium and posterior wall isolation, etc.

The treatment device 1102, 1202 can be constructed such that the treatment element 1103, 1203 can variably expanded to determine contact with the antrum, including cases of a left sided common ostium. Furthermore, as mentioned above, the segments of the treatment element 1103, 1203 in close proximity to the phrenic nerve and/or esophagus can be converted to warming segments. In some embodiments in place of or in addition to the segments, the electrodes/sensors 1108, 1208 of the treatment device 1102, 1202 can be used to create warmth regions.

In some embodiments, the treatment device 1102, 1202 can be controlled manually or robotically from a console without fluoroscopy. The treatment device 1102, 1202 can collect 3D geometry and/or identify the location of the phrenic nerve and/or esophagus. The treatment device 1102, 1202 can reconstruct the course of the phrenic nerve as a continuous variable. The various cells can be closed off (or not supplied with a solution), deflated, and/or converted to warming cells automatically to create a buffer to protect the nerve. The temperature of the tissue in contact with the phrenic nerve can be assessed and the catheter can convert more cells to warming cells if the temperature of the tissue near the esophagus gets too low or satisfies a temperature threshold. The temperature threshold can be based on a temperature at which tissue will be, or is likely to be, damaged. After the veins are isolated, the treatment device 1102, 1202 can be used to achieve a roof line, if a roof dependent tachycardia is induced.

In some embodiments, the treatment device 1102, 1202 can be used to assess for block across the roof by positioning the treatment element 1103, 1203 across the line and pacing from each side (anterior and posterior to the line). The treatment device 1102, 1202 can isolate the posterior wall of the left atrium and assess for electrical isolation. The energy modality used to achieve isolation can include, but is not limited to, cryoablation, laser, HIFU, radiofrequency, etc. An ultrasound catheter mounted to the treatment device 1102, 1202 can recreate 3D geometry, assess for leaks and coupled with the array of sensors allow for non-fluoroscopic navigation of the treatment device 1202, 1202. 3D mapping and temperature assessment of the esophagus can enhance the safety of the procedure. Segments of the treatment device 1102, 1202 adjacent to the esophagus can be turned to a warming mode to protect the esophagus.

A console can display the treatment device 1102, 1202, any portion thereof, such as treatment element 1103, 1203, or a virtual representation of thereof, and each segment of the treatment element 1103, 1203 can be independently controlled for warm mapping (low pressure), warm mapping (high pressure), cold mapping (low pressure using $N_2O$), and/or cryoablation.

By using the treatment device 1102, 1202, a healthcare provider can avoid changing catheters during surgery, i.e. from replacing the mapping device 20 with the treatment device 312. The treatment device 1102, 1202 can map in real time and also be used for ablation, thereby reducing, if not eliminating, error in accurate translation of phrenic nerve location to treatment device 1102, 1202 location. Furthermore, the treatment device 1102, 1202 can reduce the risk of inadvertent damage, reduce stress on the operator, and potentially enable the operator to be more aggressive with the ablation, due to the mapping. In cases where the distal segment 1104, 1204 is made a warm high pressure balloon, the phrenic nerve can be paced from a stable, reliable position above the treatment level. Local tissue temperature next to the nerve can be assessed. As such, the phrenic nerve can be shielded, the temperature of its local environment assessed and its function tested with the treatment device 1102, 1202.

Figure 13:
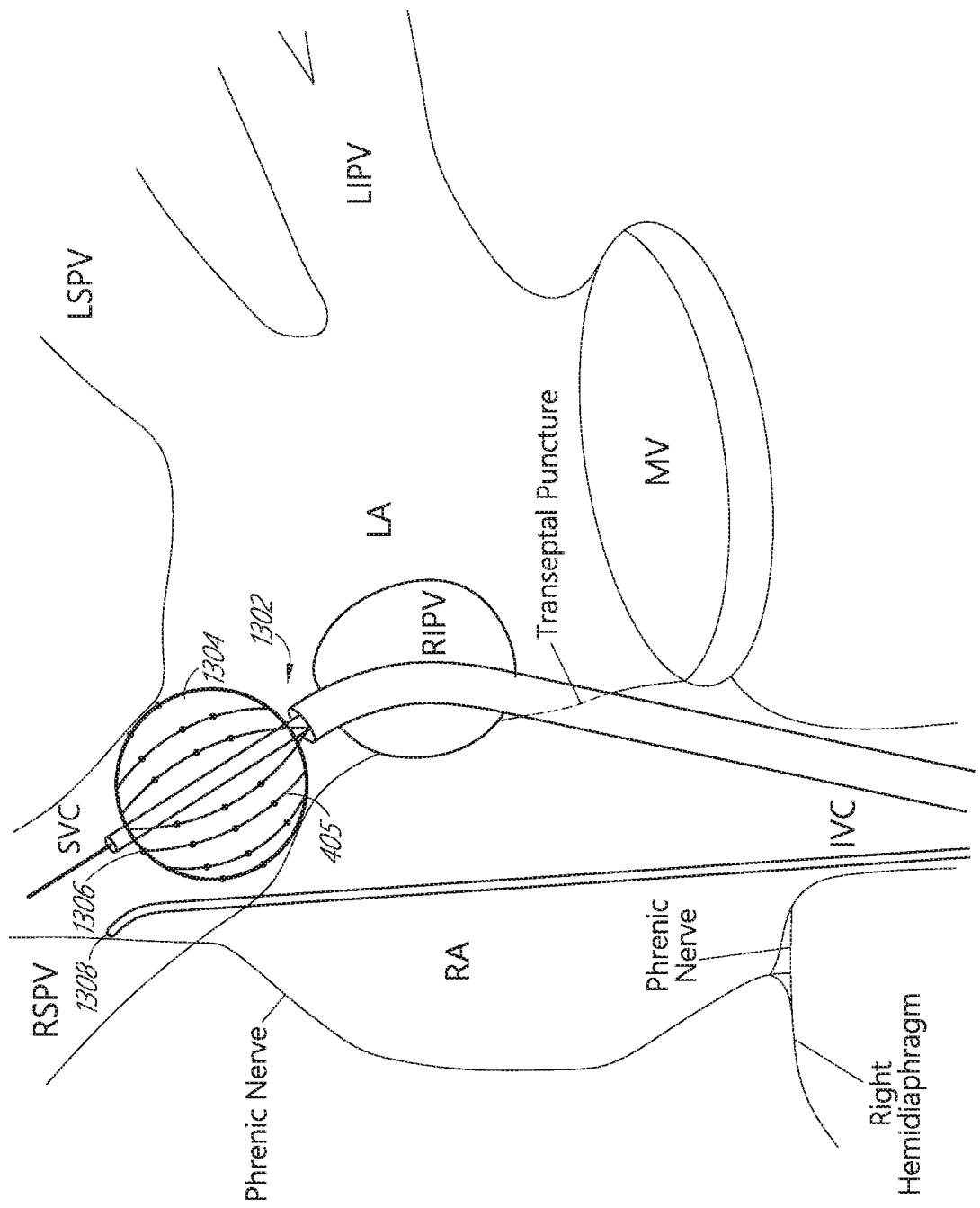
FIG. 13 is a diagram illustrative of an embodiment of a treatment device positioned within the right superior pulmonary vein.

FIG. 13 is a diagram illustrative of an embodiment of a treatment device 1302 positioned within the right superior pulmonary vein (RSPV). The treatment device 1302 can be similar to the treatment devices 1102, 1202 described previously with reference to FIGS. 11 and 12, and can include one or more treatment elements 1304 and one or more sensors 1306. The one or more sensors can also be referred to as a mapping portion 1306. The mapping portion 1306 can be similar to the mapping devices 20/402/502 and/or the sensors 1108, 1208 described previously, and the treatment element 1304 can be similar to any one or any combination of the treatment elements 326/405/505/902/1002/1103/1203, described previously.

In the illustrated embodiment, the treatment device 1302 can be placed in a mapping mode and/or a treatment mode. In the mapping mode, various electrodes of the mapping portion 1302 can be activated to determine the location of the phrenic nerve. In the treatment mode, the treatment element 1304 (or segments thereof) can be activated in order to ablate the tissue. For example, the treatment element 1304 (or segments thereof) can be filled with a coolant for cryoablation. However, as described previously, the tissue can be ablated in a variety of ways. As described in greater detail above, with reference to FIGS. 12 and 13, the segments of the treatment element 1304 can be individually and independently used as warming regions or as ablation regions.

FIG. 13 further illustrates a second catheter with a pacing electrode 1308 positioned near the phrenic nerve superior to the treatment device 1302. In some embodiments, once the treatment element 1304 is activated, the electrodes of the mapping portion 1302 may not be usable. In such embodiments, the electrode 1308 can be used to detect phrenic nerve injury, similar to the electrode 412 described previously. If a potential phrenic nerve injury is determined, the procedure can be stopped and/or different portions of the treatment device can be activated as warming regions, as described previously.

Pulmonary Vein Assessment

After each pulmonary vein has been ablated, sensing and pacing electrodes on an independent mapping array such as the Constellation Basket, complementary mapping device 502, a treatment device 1102, 1202, 1302 and a mapping overlay 1501 can be used to assess for the presence of entrance and exit block. Specifically, the presence of local electrograms (near-field signal) associated with the underlying atrial rhythm would indicate that the pulmonary vein antrum is not isolated if the integrated device is positioned opposed to the pulmonary vein antrum. The absence of signals or the presence of independent signals can indicate entrance block. Pacing of the vein from electrodes positioned distal to the ablation region can be used to assess for exit block.

Local capture of the vein can be evidenced by the generation of local PV potentials without capturing the atrium in a patient in normal rhythm can be used to determine exit block. In the case that a vein has persistent PV connection during sinus rhythm, atrial fibrillation, flutter, atrial tachycardia or other atrial rhythm, the location of the earliest local PV electrogram (near-field signal) can be mapped in both a circumferential and/or a longitudinal axis to determine the specific location of electrical entrance into the pulmonary vein antrum. Targeting this location with ablation can result in isolation of the vein and/or can reveal the presence of another site of earliest PV connection that must also be ablated to achieve isolation.

Adenosine

Adenosine, or other A1 (adenosine 1; AKA purine 1) receptor agonist, can be used post ablation in isolated veins to adjust the treatment device 1102, 1202 upon an additional treatment, such as a freeze. For example, a given pulmonary vein is isolated as determined upon remapping post ablation with the treatment device 1102, 1202. IV adenosine can be given to the point of causing transient heart block, hypotension or sinus node suppression.

A transient acute PV reconnection (as evidenced by PV electrograms associated with sinus rhythm or other atrial rhythm) can be readily and specifically targeted prior to moving to the next pulmonary vein. These acute reconnections can involve an area that leaked during ablation. Directing the treatment device to target the site(s) of acute PV reconnection can result in elimination of dormant conduction, which has been demonstrated to improve the efficacy of the atrial fibrillation ablation.

Sensors Co-Located with Treatment Element

Figure 14:
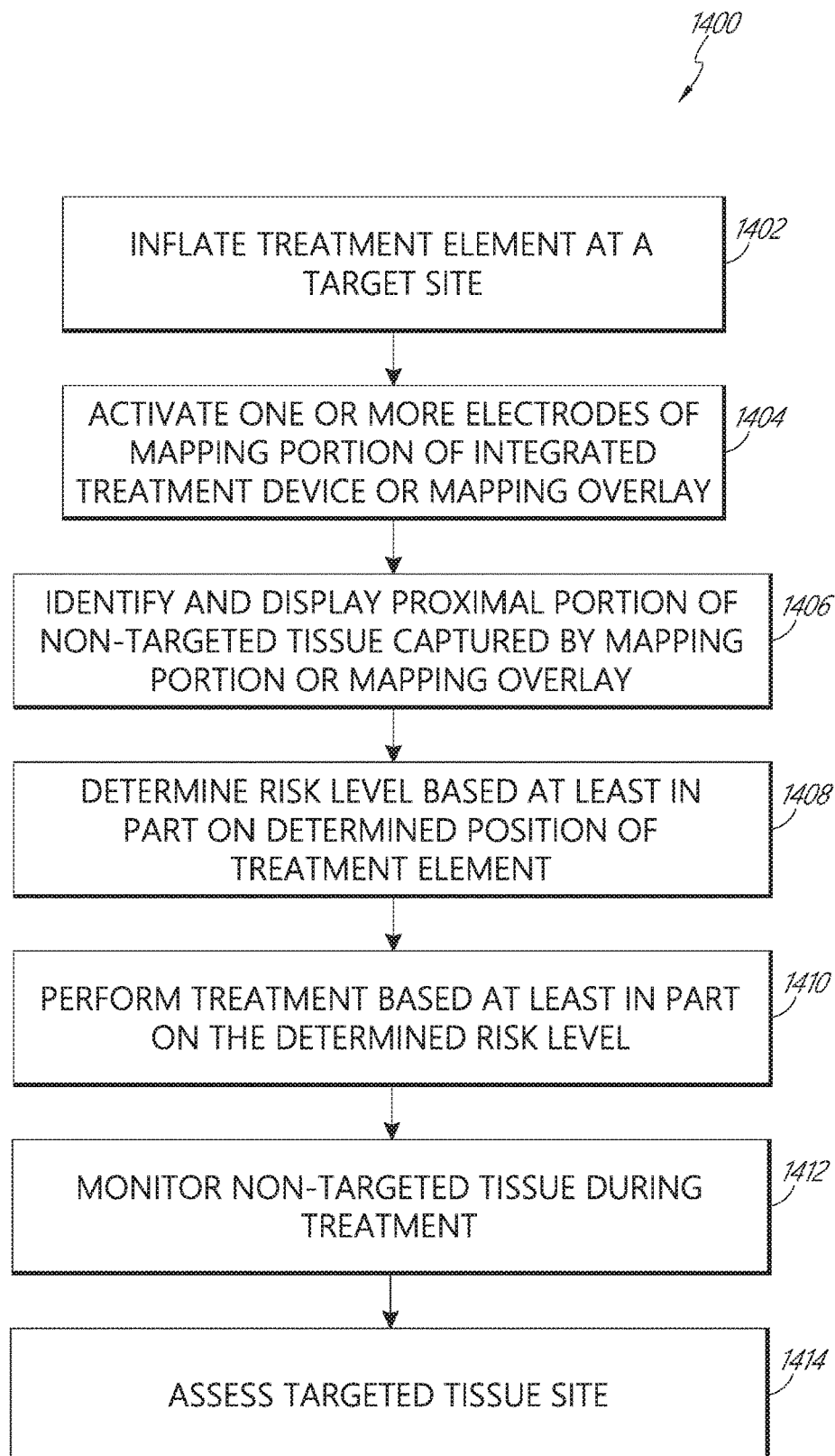
FIG. 14 is a flow diagram illustrating an embodiment of a routine for treating a tissue site.

FIG. 14 is a flow diagram illustrating an embodiment of a routine 1400 for locating non-targeted tissue near a targeted tissue site and providing treatment to the tissue site based on the location of the non-targeted tissue. In some embodiments, routine 1400 can be used in conjunction with an integrated treatment device that includes sensors co-located with a treatment element. In certain embodiments, routine 1400 can be used in conjunction with a mapping overlay or mapping device, such as the mapping overlay described below with reference to FIGS. 15A-15C and 16A-16C, that is distinct from a treatment device but provides sensors or electrodes that are co-located with at least a portion of the treatment element of a treatment device.

At block 1402, a treatment element of a treatment device is inflated at a targeted tissue site, which can also be referred to as a target site or treatment site. In some embodiments, the tissue site can be the pulmonary vein. In some embodiments, prior to inflation, the treatment element is placed in the pulmonary vein antrum and an occlusive balloon venogram is performed to determine its location.

At block 1404, one or more electrodes of a mapping portion of the integrated treatment device or a mapping overlay (as described in greater detail in FIGS. 15A-15C and 16A-16C) coupled to a treatment device are activated to determine the location of a proximal portion of tissue near the target site, such as the phrenic nerve in the pulmonary vein.

At block 1406, the proximal portion of the non-targeted tissue near the target site captured by the mapping portion or mapping overlay is identified and displayed. In some embodiments, it is determined whether a proximal portion of the mapping portion or mapping overlay is free of non-targeted tissue stimulation, such as phrenic nerve stimulation. If not, the device can be retracted until the mapping portion corresponding to the location of the treatment element is free of non-targeted tissue capture. In certain cases, such as when used to treat cardiac arrhythmia, this can reduce the likelihood that phrenic nerve function will be affected by the treatment element.

At block 1408, a risk level is determined based at least in part on the position of the treatment element relative to the identified proximal portion of the tissue near the target site. In some embodiments, zones to be treated and zone of non-targeted tissue to be protected can be established.

At block 1410, treatment is performed at the target site based at least in part on the determined risk level. As described in greater detail above with reference to FIG. 7, in some embodiments, if the risk level is determined to be high, the treatment element can be moved and/or one or more segments or electrodes can be used to protect the non-targeted tissue. For example, one or more segments can be deflated or used as a warming balloon, etc.

At block 1412, the non-targeted tissue is monitored during treatment. For example, the non-targeted tissue can be monitored by electrical stimulation or other methods. If an adverse reaction is detected, the treatment element can be moved or the treatment stopped.

In embodiments in which the phrenic nerve is paced, during the ablation, if a reduction of the force of diaphragmatic contraction is detected by palpation, the position of the catheter in the SVC can be verified. If the location was identified as low risk and the catheter pacing the phrenic nerve has moved, the fluoroscopy can be repositioned. If a weakening of the diaphragm is detected fluoroscopically, the treatment element can be forcibly deflated and the ice shell fractured with saline administered through the distal port. If the diaphragm is moving normally on fluoroscopy, the treatment element can be repositioned in the SVC to regain phrenic nerve capture and the ablation continued. If the case was identified as intermediate risk and the diaphragmatic contraction weakens by palpation, the treatment element can be deflated and the ice shell fractured. Fluoroscopy can be performed to assess the motion of the right hemidiaphragm.

At block 1414, the targeted tissue site is assessed, and in certain cases, additional treatment provided. In some embodiment, once an initial treatment is completed, the tissue at the targeted tissue site can be examined to determine whether additional treatment is to be provided. For example, electrical signals near the targeted tissue site can be monitored.

With respect to embodiments in which cardiac arrhythmia is being treated, the presence of PVI can be assessed. In some embodiments, PVI can be assessed using the mapping portion of the integrated treatment device, evaluating for the presence of local PV electrograms to determine the presence of entrance block, and pacing the pulmonary vein to determine the presence of exit block. In response, if persistent PV conduction is detected, additional treatment can be provided. For example, in some cases, the earliest site of entrance conduction into the PV/PV antrum can be targeted with the treatment device. Additional sites can be treated based on additional assessments for PVI. In addition, as part of the assessment, adenosine can be administered after PVI to determine the presence of dormant conduction. Following the administration of the adenosine, if PV conduction is detected, additional treatment can be provided. For example, the earliest site of entrance conduction into the PV can be targeted with the treatment device. In some cases, the presence of PVI can be repeatedly assessed until there is no evidence of dormant conduction.

Fewer or more steps can be included as desired. For example, if the risk level is high or intermediate, the treatment element can be moved, distal portions of the treatment element can be deflated and/or used as warming portions, and/or electrodes can be activated to create a warming region, etc. In addition, during treatment for cardiac arrhythmia, the phrenic nerve can be monitored, etc. Furthermore, it will be understood that any one or any combination of the steps described above with respect to FIGS. 7 and 8 can be used. For example, multiple images can be taken at different times and at different orthogonal views, etc.

In addition, although specific embodiments are described with respect to identifying the location of the phrenic nerve during treatment of cardiac arrhythmia, it will be understood that routine 1400 can be used to identify non-targeted tissue near targeted tissue sites during treatment of other areas of the body. For example, the greater and lesser cavernous nerves (non-targeted tissues) pass nearby the prostate gland and can be injured during prostate surgery causing erectile dysfunction. By identifying the location of the nerves prior to treatment, the likelihood of injury can be reduced.

Mapping Overlay

Figure 15A:
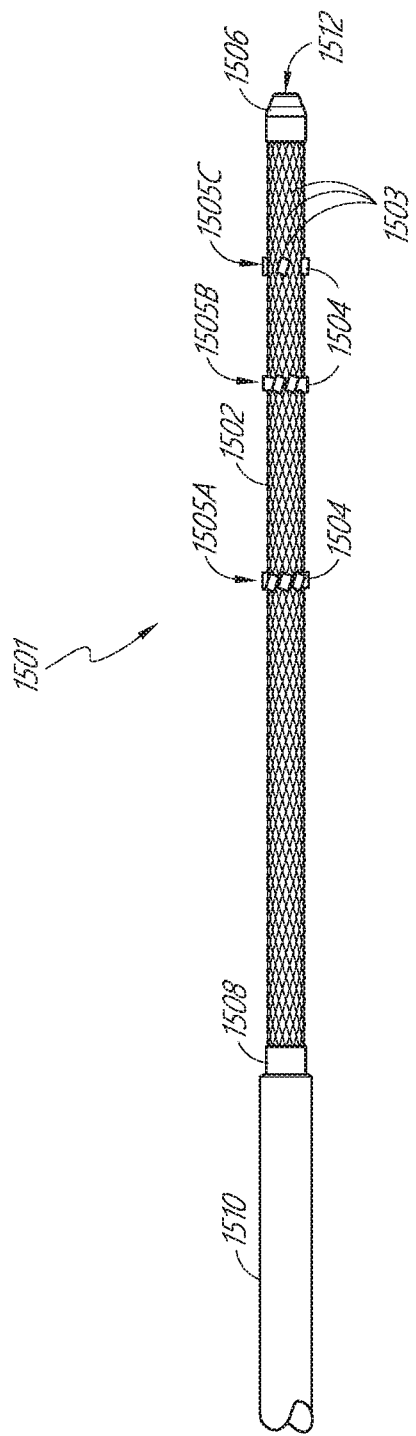
FIGS. 15A-15C are diagrams illustrative of a mapping overlay.
Figure 15C:
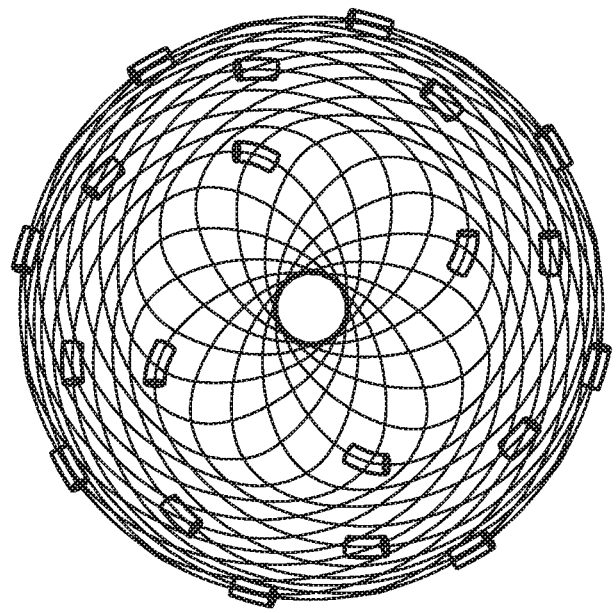
Figure 15B:
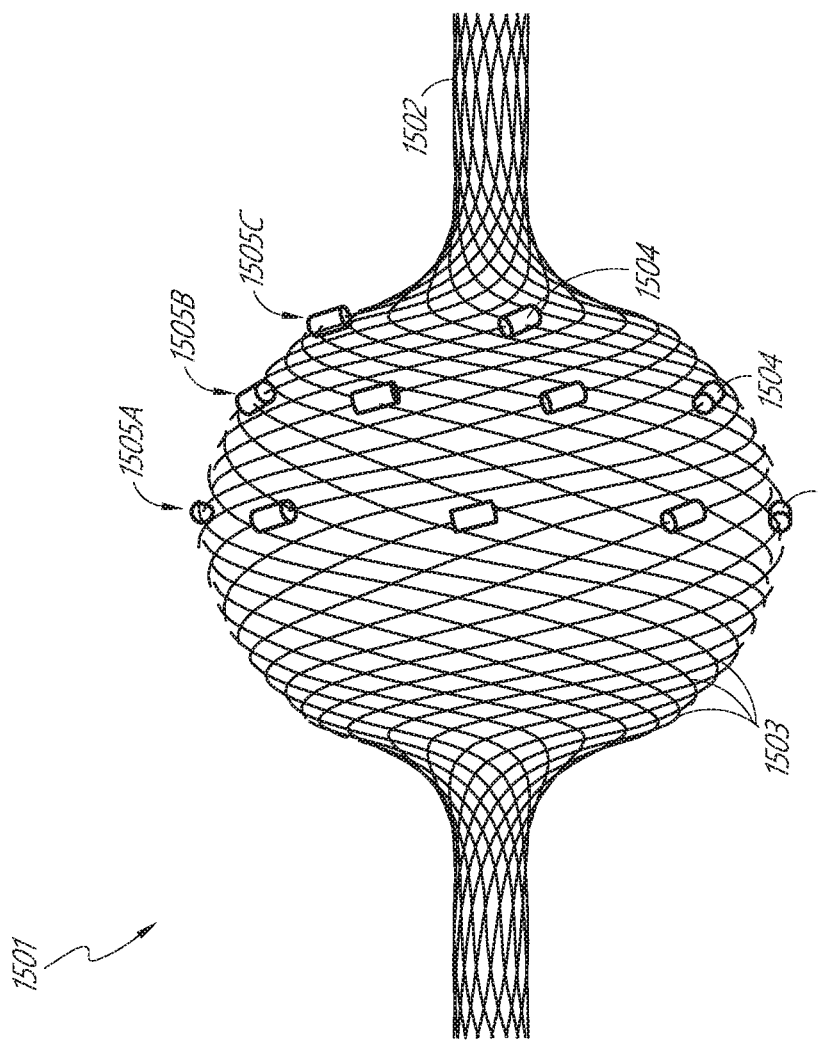

FIGS. 15A-15C are diagrams illustrative of a mapping overlay 1501, which can form part of a mapping device or mapping catheter. The mapping overlay 1501 can be used in association with a treatment device, such as the treatment devices 312, 404, 504, form part (e.g., the mapping portion) of the integrated treatment devices 1102, 1202, 1302, and/or be used in any one or any combination of the routines 700, 800, and/or 1400.

In the illustrated embodiment, the mapping overlay 1501 includes a wire mesh 1502 extending beyond a catheter body 1508, which can also be referred to as a lining or tube, and multiple sensors/electrodes 1504 (individually referred to as sensor/electrode 1504). A distal end of the mesh 1502 can be coupled to a cap 1506 and a proximal portion of the mesh 1502 can be coupled to, or encircled by the body 1508. In some embodiments, an interior diameter of the mesh 1502 can be sized to enable a treatment device, such as treatment devices 312, 404, 504 to pass therethrough. In certain embodiments, an exterior diameter of the mesh 1502 and body 1508 can be sized to pass within an inner diameter of a sheath 1510.

The mesh 1502 can include a plurality of interwoven or braided wires 1503 (individually referred to as a wire 1503). In certain embodiments, the mesh can form a tubular structure. In some embodiments, the wires 1503 can be wound helically and form a perimeter of a lumen. In certain cases, the mesh can include longitudinal wires running lengthwise with the lumen and woven wires that weave between the longitudinal wires. In some cases, the wires can be interlaced with each other like a braid. Any number of wires 1503 can be used for the mesh 1502. In some cases, the mesh 1502 can be cylindrical with an interior lumen. However, it will be understood that the mesh 1502 can be formed in any shape. In some embodiments, the minimum number of wires 1503 is equal to at least the number of electrodes 1504 used with the mesh 1502 or twice the number of electrodes 1504 used with the mesh 1502. For example, if 32 electrodes 1504 are attached to the mesh 1502, the mesh can be made up of 32 wires 1503 or 64 wires 1503. However, it will be understood that the mesh 1502 can include fewer or more wires 1503 as desired.

In some embodiments, the wires 1503 of the mesh 1502 can be made of steel, coated copper polyester, nitinol, composite material, platinum, platinum coating over nitinol core, tungsten (strength), or other biocompatible metal or conductor. In some embodiments, the wires can be multi-conductor wires or cables (non-limiting examples: coaxial cable with one more cores, multi-ribbon wire, etc.). Further, the wires 1503 can be coated in Teflon, polyester polyimide kapton, or other biocompatible electrical insulator, such as plastic, etc.

In some cases, the mesh 1502 can include a combination of different types of wires 1503. For example, the mesh 1502 can include a one or more conductor wires, one or more structural wires, and/or one or more radiopaque wires. The different wires can be made of different material and can be braided together to provide the mesh 1502 with different characteristics. For example, the conductor wires (non-limiting examples: copper) can be used to provide an electrical signal to and/or from the sensors 1505, the structural wires (non-limiting examples: steel, nitinol, tungsten) can be used to provide the mesh 1502 with rigidity and structure, and the radiopaque wires (non-limiting examples: tungsten, platinum, gold-plated) can be used to increase the visibility of the mesh 1502 when inserted into a patient. In certain cases, the sensors 1504 are coupled only to the conductor wires and are not coupled to the structural wires or the radiopaque wires. In certain cases, a conductor wire can also be used as a structural and/or radiopaque wire. In some cases, the majority of the wires of the mesh 1502 can be conductor wires. In certain embodiments, approximately one fourth of the wires can be structural wires. However, it will be understood that the mesh can include any combination of conductor wires, structural wires, and/or radiopaque wires.

The mesh 1502 can be constructed to expand/collapse passively or actively. To expand passively, the mesh 1502 can rely on a force applied to it from another object proximate thereto, such as a treatment element of a treatment device. For example, in some embodiments, as the treatment element enlarges, it can exert a deformation force on the wires 1503. In response to the deformation force, the wires 1503 can deform and the mesh 1502 expand, as illustrated in FIG. 15B.

Similarly, to collapse passively, the mesh 1502 can rely on a force applied to it from another object proximate thereto, such as the sheath 1510. In some embodiments, once the deformation force from the treatment element is withdrawn due to a deflation and/or removal of the treatment element, the mesh 1502 can retain the shape created by the deformation force of the treatment element, or otherwise not return to its pre-deformed shape absent an additional force. In such embodiments, if the mesh is in an expanded state (as shown in FIG. 15B) due to a previous deformation force applied thereto by a treatment element, the mesh 1502 can be passively collapsed using a force applied thereto by the sheath 1510. For example, as the mapping overlay 1501 is withdrawn from the target site and pulled through the sheath 1510, a deformation force on the mesh 1502 from the sheath 1510 can cause the mesh 1502 to deform back to a predetermined shape or a shape similar to the predetermined shape.

In some embodiments, the mesh 1502 can collapse passively based on the pliability characteristics of the wires 1503. For example, the wires 1503 can be constructed to have sufficient spring such that once a deformation force, such as from a treatment element, is removed from the wires 1503, the wires 1503 return to a predetermined shape or similar thereto. In some cases, the wires 1503 can return to a predetermined shape unless a deformation force that satisfies a wire pliability threshold is applied. If the deformation force satisfies the wire pliability threshold, the wires 1503 can maintain their new shape or not return to the predetermined shape.

To expand or collapse actively, the wires 1503 can be controlled by a user. For example, the user can manipulate a lever or knob to actively adjust the expansion and/or collapse of the wires. The lever or knob can enable the user to expand or collapse the mesh 1502 as desired. For example, moving a lever or slider button in one direction, such as a longitudinal axis of the mapping overlay can cause the mesh 1502 to expand and moving the lever or slier button in a different direction, such as an opposite direction, can cause the mesh 1502 to collapse.

In some embodiments, to form the mapping overlay or mapping catheter, an inner layer, such as a polymer or other flexible material, can be heat shrunk, or otherwise coupled or bonded, around a tube, such as a mandrel. One or more wires 1503 with or without electrodes can be pre-braided in a tubular structure and slid over the first layer on the mandrel to form a second layer. The mesh of wires 1502 can extend past a distal end and proximal end of the inner layer and the mandrel. A third layer can be laminated over the portion of the wires that that are on top of the mandrel. To provide structural or mechanical properties such as flexibility, pushability, and torqueability, other layers can be added to control said properties. After the layers are placed over the wires 1503, the mandrel can be removed. Accordingly, a distal portion of the mapping catheter can include the mesh of wires without an inner layer or outer layer, the middle portion (or body 1508) of the mapping catheter can include the mesh of wires sandwiched between the inner layer and outer layers of material, and a proximal portion of the mapping catheter can include the mesh 1502. In some embodiments, 6-12" of mesh can extend beyond the body 1508 of the mapping catheter at both the distal end and proximal end. However, it will be understood that the mapping overlay can be configured to have more or less mesh extend beyond the body 1508. Furthermore, it will be understood that the mapping overlay can be constructed in a variety of ways. As another example, the body 1508 can extend along the entire length of the mesh 1502. A distal end of the body 1508 and mesh 1502 can be dipped in acid to remove the inner and outer layers of the body 1508 from the mesh 1502, etc.

In some embodiments, the mesh 1502 can provide a known spatial relationship between the electrodes 1504. In addition, the mesh 1502 can provide the mapping overlay with flexibility and radial control, which can increase the likelihood of an accurate mapping of surrounding tissue.

With continued reference to FIGS. 15A-15C, one or more sensors and/or electrodes 1504, described in greater detail above, can be coupled to the mesh 1502. A sensor/electrode 1504 can be coupled to a wire 1503 by using a biocompatible adhesive, bonding agent, welding, soldering, plated over exposed copper, or other coupling that is biocompatible and electrically conductive, etc. In some cases, to apply a sensor and/or electrode to a wire 1502, a portion of the insulation of the wire can be removed. The exposed portion of the wire can be gold plated or have a stainless metal applied as the electrode 1504. In certain cases, a portion of the wire 1502 can be cut and a resistive material can be applied to provide a heating electrode.

In some cases, a single sensor/electrode 1504 can be coupled to (only) one of the wires 1503 of the mesh 1502. For example, a wire 1503 with a sensor/electrode 1504 can terminate at the cap 1506. In such embodiments, the wire 1503 and electrode 1504 can act as a passive sensor or voltmeter. In certain cases, a sensor/electrode 1504 can be coupled to more than one wire 1503. For example, the sensor/electrode 1504 can be affixed to a first wire carrying an electrical signal to or from a controller. The first wire can be electrically coupled to a second wire to carry the signal in the opposite direction as the first wire (non-limiting example: first wire carries electrical signal distally from controller and second wire carries electrical signal back to the controller, or vice versa). In some embodiments, more than one sensor/electrode 1504 can be coupled to a single wire 1503. In embodiments, where more than one electrode 1504 is coupled to a wire, the wire can be a multi-conductor wire and/or the electrodes 1504 can be read using multiplexing. The wire(s) 1503 coupled to the relative sensor/electrode 1504 can provide the sensor/electrode 1504 with an electrical connection thereby enabling the control of the sensor/electrode 1504 and the ability to receive data from the sensor/electrode 1004.

Additionally, in some embodiments, the wire(s) 1503 can keep the sensor/electrode 1504 in place. For example, the mesh 1502 can provide a 3D fixation for the sensor/electrode 1504. As such, the location of the sensor/electrode 1504 relative to the treatment device can be known with greater accuracy and/or dependability.

When more than one sensor/electrode 1504 is used, the sensors/electrodes can be located in a variety of configurations. In some embodiments, the sensors/electrodes 1504 can be evenly (or unevenly) spaced from each other. In certain embodiments, the sensor/electrodes 1504 can be located on the mesh 1502 such that they are distal to or (approximately, such as ±5 cm) coaxial with the portion of a treatment element of a treatment device with the largest circumference or perimeter when the treatment element is expanded (e.g., the meridian of the treatment element). However, it will be understood that the sensor/electrodes 1504 can located anywhere on the mesh 1502. For example, one or more sensor/electrodes 1504 can be located proximal to the meridian of the treatment element. Similarly, the sensor/electrodes 1504 can be located along an entire portion of a treatment element of a treatment device and/or distal or proximal to the treatment element of a treatment device.

In some embodiments, the sensors/electrodes 1504 can be arranged into one or more groups 1505A, 1505B, 1505C of sensors/electrodes 1504. For example, multiple sensors/electrodes 1504 can be located at approximately the same distance from the cap 1506 such that a group (e.g., groups 1505A, 1505B, 1505C) of sensors/electrodes 1504 form a ring. In such an embodiment, when the treatment element of a treatment device is enlarged (as shown in FIGS. 15B, 15C), the group 1505A, 1505B, 1505C of sensors/electrodes 1504 can form a ring around a particular portion of the treatment element, such as a particular circumference or perimeter around the treatment element. In the illustrated embodiment of FIG. 15, the sensor/electrodes 1504 are arranged into three groups 1505A, 1505B, 1505C. The sensor/electrodes 1504 within a group 1505A, 1505B, 1505C can be the same type of sensor/electrode 1504 and/or a combination of different sensor/electrodes 1504.

Furthermore, in some embodiments, one group of sensor/electrodes 1504 can be offset with respect to a proximate group of sensor/electrodes 1504. For example, in the illustrated embodiment of FIG. 15, the group 1505A of sensor/electrodes 1504 is offset with respect to the group 1505B of sensor/electrodes 1504 such that if all of the sensor/electrodes 1504 of groups 1505A, 1505B were on the same axis, the sensor/electrodes 1504 from group 1505B would be in between the sensor/electrodes 1504 of group 1505A. In certain embodiments, the groups of sensor/electrodes 1504 are not offset, such that if all of the sensor/electrodes 1504 were on the same axis, a sensor/electrode 1504 from group 1505B would be co-located with a sensor/electrode 1504 of group 1505A.

The cap 1506 can be coupled with a distal portion of the mesh 1502. In some embodiments, a distal portion of the wires 1503 can be coupled to the cap 1506. For example, an end of each wire 1503 can be may be adhered or bonded to the cap 1506 using a biocompatible adhesive, bonding agent, welding, soldering, crimping, etc. As yet another example, a portion of the wire 1503, such as an end or middle portion, can be wound around the cap 1506 or inserted through a hole in the cap 1506. In some embodiments, the cap 1506 can provide electrical connections between wires 1503 to enable a completed circuit to be formed for each sensor/electrode 1504. In some cases, the cap can include an inner lumen large enough to fit a guidewire. For example, the inner lumen can be between 0.032"-0.035" in diameter. It will be understood that lumen's diameter can be other widths as well.

In certain embodiments, the cap 1506 can include an inner portion and an outer portion. The inner portion can be used to couple the cap 1506 to the mesh 1502 and to the treatment device. The outer portion can cover the inner portion to protect the interconnections from the environment and can have an atraumatic shape to avoid damaging the tissue when inserted into a patient. In some embodiments, the cap 1506 can include a central lumen 1512. The central lumen 1512 can be sized for a guidewire or portion of a treatment device. In some embodiments, the central lumen 1512 can include a sphincter that can be broken when the treatment device is inserted.

In addition, the cap 1506 can be coupled with a distal end of the treatment device. For example, the cap 1506 can include a protrusion or indentation that can be used to engage with the treatment device to prevent unwanted relative movement between the mapping overlay and the treatment device when the treatment device is in use. In some cases, an interior portion of the cap 1506 can include threads that can engage with a distal end of the treatment device. The cap 1506 and the treatment device can be disengaged by twisting and/or pulling the two apart.

The body 1508 can be made of one or more layers of polymer or other flexible material. In some embodiments, the body 1508 can be coupled with a proximal portion or middle portion of the mesh 1502. For example, as described above, the body 1508 can include one or more inner layers of polymer and one or more outer layers of polymer and a portion of the mesh 1502 can be located between the inner/outer layer(s).

In certain embodiments, a proximal portion or middle portion of the mesh 1502 can be located within the body 1508 and/or sandwiched between layers of the body 1508. In some cases, the mesh 1502 can extend at least along the length of the body 1508 within the sheath 1510. In some embodiments, the mesh 1502 can extend beyond a distal end of the body 1508, as illustrated in FIG. 15A. Furthermore, the mesh 1502 can extend beyond a proximal end of the body 1508 (not shown).

The outer portion of the body 1508 can be coated in Teflon, hydrogel, or other lubricious material, to reduce the amount of friction between the body 1508 and an outer sheath 1510. In certain embodiments, the body 1508 can also include a junction box for receiving the electrical signals from the sensors. The junction box can be located at a proximal end of the body 1508 that is not inserted into a patient during a procedure.

When the mesh 1502 expands either passively or actively, its length can decrease. In some embodiments, as the length decreases, the body 1508 can be pulled towards the cap 1506.

FIGS. 15B and 15C are diagrams illustrating the mesh 1502 of the mapping overlay 1501 in an expanded state, which can be caused by the enlargement of a treatment element of a treatment device. As described above, in the expanded state, the sensor groups 1505A, 1505B, 1505C can form a ring around different portions of the treatment element of the treatment device. FIGS. 15B and 15C further illustrate the helical nature of the windings of the wires 1503 and the coupling between a sensor 1504 and a wire 1503.

Figure 16C:
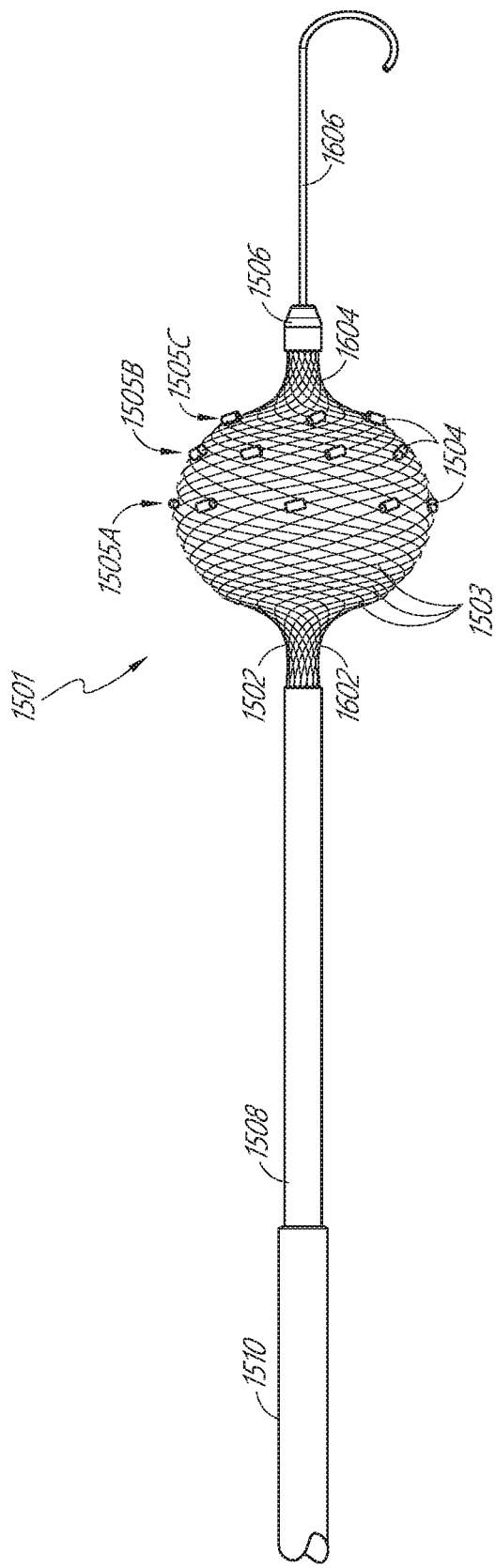

FIGS. 16A-16C are diagrams illustrating embodiments of the mapping overlay 1501 and a treatment device 1602 in different configurations and positions. The treatment device 1602 can be similar to the treatment devices 312, 404, 504 described previously and can include a treatment element 1604 to treat a target site.

In some embodiments, the mapping overlay 1501 and treatment device 1602 can be implemented as part of a single catheter. In certain embodiments, the mapping overlay 1501 and the treatment device 1602 can be implemented as separate devices, such as two distinct catheters and/or a sheath and a catheter. For example, the mapping overlay 1501 can be sized such that the treatment device 1602 fits within an inner lumen of the mapping overlay 1501.

In the illustrated embodiment of FIG. 16A, the sheath 1510 is shown with the cap 1506 of the mapping overlay 1501 protruding from a distal portion thereof. The illustrated configuration of FIG. 16A can represent a scenario in which the sheath 1510 has been placed at a target site or proximate to a target site and the mapping overlay 1501 and/or the treatment device 1602 have been guided to the target site by the guidewire 1606 through the sheath 1510. For example, in a cardiac ablation procedure, the sheath 1510 can be inserted near the groin and follow the femoral vein and inferior vena cava to the heart and the mapping overlay 1501 and treatment device 1602 can be inserted inside the sheath 1501 and follow the sheath 1501 to the heart. A non-limiting example of a sheath is the FlexCath® Steerable Sheath available from Medtronic. Destino Twist® deflectable steerable guiding sheath from Oscor; Agilis NXT steerable introducer sheath from St. Jude; etc.

In the illustrated embodiment of FIG. 16B, the mapping overlay 1501 and the treatment device 1602 are visible protruding from the sheath 1510. The configuration illustrated in FIG. 16B can represent a scenario in which a user is preparing to treat the target site. In the illustrated embodiment, the treatment device 1602 including the treatment element 1604 is visible within the mesh 1502 of the mapping overlay 1501. As described in greater detail above, the treatment element 1604 can be used to treat the target site using RF, HIFU, laser, hot balloon, and/or cryotherapy. In some embodiments, the mapping overlay 1501 can be sized such that it generally extends across the entire length of the treatment element 1604.

In the illustrated embodiment of FIG. 16C, the treatment element 1604 of the treatment device 1602 is shown in an expanded state. The configuration illustrated in FIG. 16C can represent a scenario in which a user has filled the treatment element with a gas in preparation for treating the target site. In such a configuration, the mapping overlay 1501 can be used to map the target site and/or to monitor the effect of treatment on the target side, as described in greater detail above. As a non-limiting example, the sensor/electrodes 1504 can be used to pace tissue at the target site, such as a phrenic nerve, monitor a temperature at the target site, etc.

As illustrated in the FIG. 16C, when the treatment element 1604 is enlarged, the mesh 1502 in the area of the treatment element can expand as well. The expansion of the mesh 1502 where the treatment element 1604 portion can induce a force on the remaining portion of the mesh 1502 which can pull the body 1508 further out from the sheath 1510. Accordingly, in some embodiments, the interior of the sheath 1510 and the exterior of the body 1508 can be constructed to have a low friction coefficient such that the body 1508 can slide with relative ease when treatment element 1604 is expanded.

Furthermore, as described in greater detail above, the wires 1503 of the mesh 1502 can be constructed to achieve a particular level of pliability such that when the treatment element 1604 is deflated, the mesh 1502 can retain its expanded shape. In such an embodiment, the mesh 1502 can retain the expanded shape until pulled inside the sheath 1510. The force exerted on the mesh 1502 by the sheath 1510 can flatten the mesh 1502 back to a predetermined shape or similar to a predetermined shape. It will be understood, however, that the mesh 1502 can be constructed so that when the treatment element is reduced in size and/or removed, the mesh 1502 can return to its predetermined shape or similar thereto In some embodiments, the mapping overlay 1501 and treatment device 1602 can be placed within an outer sheath and can be independently operated. For example, the mapping overlay 1501 can be independently moved. Similarly, the treatment device 1602 and treatment element 1604 can be independently moved, collapsed, and/or expanded as desired.

Although described above as being distinct from the treatment device 1602, it will be understood that in some embodiments, the mapping overlay 1502 can be permanently affixed to or form part of the treatment device 1602. For example, the mapping overlay 1502 can form part of an integrated treatment device, similar to integrated treatment devices 1102, 1202, 1302, described in greater detail above. In such embodiments, the treatment device can include the treatment element 1604, the mesh 1502 and/or the sensors 1504. In addition, the mapping overlay can be used in any one or any combination of the routines 700, 800, and/or 1400 described above.

Furthermore, it will be understood that the various embodiments described herein can be combined in any fashion. For example, a mapping overlay can be used in conjunction with any one or any combination of the treatment device embodiments.

Non-Limiting Embodiments

Various example embodiments of the disclosure can be described in view of the following clauses:

Clause 1. A method for ablating tissue, the method comprising:
 activating one or more electrodes of a mapping device to stimulate non-targeted tissue proximate a target tissue site;
 determining a location of at least a proximal portion of the non-targeted tissue based at least in part on said activating;
 determining a risk level associated with treatment of the target tissue site based at least in part on the determined location of the proximal portion of the non-targeted tissue; and
 treating tissue at the target tissue site using a treatment device based at least in part on the determined risk level.

Clause 2. The method of clause 1, wherein the non-targeted tissue comprises a phrenic nerve, the target tissue site comprises a pulmonary vein, the treating comprises ablating the tissue, and the treatment device comprises an ablation device.

Clause 3. The method of any of clauses 1 and 2, wherein the proximal portion of the phrenic nerve comprises the portion of the phrenic nerve that is closest to a junction of a pulmonary vein and left atrium.

Clause 4. The method of any of clauses 1-3, wherein the electrodes are located on an exterior portion of the treatment device.

Clause 5. The method of any of clauses 1-4, wherein the mapping device forms at least a portion of a mapping catheter and the treatment device forms at least a portion of an ablation catheter that is distinct from the mapping catheter.

Clause 6. The method of any of clauses 5, wherein at least a portion of the ablation catheter is positioned within a lumen of the mapping catheter.

Clause 7. The method of any of clauses 1-6, wherein the mapping device comprises a mesh of braided wires and the one or more electrodes comprises a plurality of electrodes coupled to the braided wires.

1. The method of any of clauses 1-7, wherein the mapping device further comprises a body, the body comprising:
 one or more inner layers, and
 one or more outer layers,
  wherein at least a portion of the braided wires is located between the one or more inner layers and the one or more outer layers, and the braided wires extends past a distal end of the body.

Clause 8. The method of any of clauses 1-8, wherein the mapping device further comprises a cap coupled to a distal end of the mesh of braided wires.

Clause 9. The method of any of clauses 1-9, wherein the treatment device comprises a cryoablation balloon and the electrodes are located on the exterior of the cryoablation balloon.

Clause 10. The method of any of clauses 1-10, wherein said activating comprises sequentially activating the one or more electrodes along a perimeter of the mapping device.

Clause 11. The method of any of clauses 1-11, wherein said activating comprises sequentially activating the one or more electrodes along a wire of the mapping device.

Clause 12. The method of clause 5, wherein at least a portion of the mapping catheter is positioned within a lumen of the ablation catheter.

Clause 13. The method of any of clauses 1-13, further comprising
 determining a location of the mapping device timed to a particular portion of an anatomical cycle; and
 determining a location of the ablation device timed to the particular portion of the anatomical cycle,
  wherein the risk level is further determined based at least in part on the determined location of the mapping device and the ablation device timed to the particular portion of the anatomical cycle.

Clause 14. A method for ablating tissue, the method comprising:
 providing a mapping device at a first tissue location proximate an atrium of a heart of a patient;
 sequentially activating one or more electrodes of the mapping device to pace a phrenic nerve;
 determining a location of a most proximal portion of the phrenic nerve to the atrium based at least in part on said activating and on monitoring a diaphragmatic contraction of the patient;
 providing a treatment device at the first tissue location based at least in part on the determined location of the most proximate portion of the phrenic nerve; and
 ablating tissue at the first tissue location based at least in part on a determination that an active region of the treatment device satisfies a distance threshold with respect to the most proximal portion of the phrenic nerve.

Clause 15. A mapping catheter comprising:
 a mapping device, comprising:
 a plurality of wires, and
 a plurality of electrodes, at least one electrode located on each tine; and
 a control device, wherein the control device is configured to alter a configuration of the mapping device between a collapsed configuration, an expanded configuration, and a treatment configuration.

Clause 16. The mapping catheter of clause 16, wherein the control device is coupled to a runner that advances or retracts based at least in part on movement of the control device, and wherein at least a portion of each tine is coupled to the runner.

Clause 17. A treatment device, comprising:
a treatment element; and
a mapping portion including a plurality of sensors located on an exterior portion of the treatment element.

Clause 18. The device of clause 18, wherein the treatment element comprises a proximal balloon and a distal balloon that is smaller than the proximal balloon.

Clause 19. The device of any of clauses 18 and 19, wherein the plurality of sensors are located on an exterior portion of the proximal balloon and the distal balloon.

Clause 20. The device of clause 19, wherein the treatment element further comprises a third balloon that encapsulates the proximal balloon and the distal balloon.

Clause 21. The device of any of clauses 19-21, wherein the proximal balloon and the distal balloon are independently inflatable/deflatable.

Clause 22. The device of any of clauses 19-22, wherein the proximal balloon and the distal balloon are independently fillable with a cooling agent or a warming agent.

Clause 23. The device of any of clauses 1-23, wherein the proximal balloon comprises a plurality of segments.

Clause 24. The device of clause 24, wherein each of the plurality of segments are independently fillable with a cooling agent or a warming agent.

Clause 25. The device of any of clauses 18-25, wherein the plurality of sensors comprise at least one of a pacing/sensing electrode, a radiofrequency electrode, a flow sensor, a temperature sensor, an optical sensor, or a force sensor.

Clause 26. The device of any of clauses 18-26, wherein the plurality of sensors comprise a plurality of electrodes configured to provide an electrical pulse to determine a location of a phrenic nerve and different portions of the treatment element are activated based at least in part on the determined location of the phrenic nerve.

Clause 27. A method for placing catheters, the method comprising:
providing a first medical device at a first tissue location of a patient timed to a particular portion of an anatomical cycle of the patient;
performing a first medical diagnostic and/or procedure with the first medical device;
moving the first medical device to a second location;
providing a second medical device at the first tissue location timed to the particular portion of the anatomical cycle; and
performing a second medical diagnostic and/or procedure with the second medical device.

Clause 28. The method of clause 28, wherein moving the first medical device comprises removing the first medical device from a patient.

Clause 29. The method of any of clauses 28 and 29, further comprising imaging the first medical device at the first tissue location timed to the particular portion of the anatomical cycle.

Clause 30. A method for ablating tissue, the method comprising:
providing a mapping device at a first tissue location within a heart of a patient;
determining a location of the mapping device at the first tissue location timed to a particular portion of a respiration cycle of the patient;
determining a location of a phrenic nerve of the patient using the mapping catheter;
moving the mapping device to a second location;
providing a treatment balloon at the first tissue location;
determining a location of the treatment balloon at the first tissue location timed to the particular portion of the respiration cycle of the patient; and
ablating tissue at the first tissue location based at least in part on a determination that an active region of the treatment balloon satisfies a distance threshold with respect to the phrenic nerve when timed to the particular portion of the respiration cycle of the patient.

Clause 31. The method of clause 31, further comprising displaying the location of the phrenic nerve on an image of the first tissue location timed to the particular portion of the respiration cycle of the patient, wherein the determination that the cryoablation balloon is proximal to the phrenic nerve with respect to the catheter is based at least in part on a comparison of the determined location of the phrenic nerve with respect to the determined location of the cryoablation balloon.

Clause 32. A mapping overlay for a treatment device, the mapping overlay comprising:
a mesh of wires; and
a plurality of sensors coupled to the mesh of wires, wherein the mesh of wires forms a lumen for a treatment device.

Clause 33. The mapping overlay of clause 33, wherein the plurality of sensors comprise at least one of a temperature sensor or a pacing electrode.

Clause 34. The mapping overlay of any of clauses 33 and 34, wherein the plurality of sensors are grouped into two or more rings of sensors.

Clause 35. The mapping overlay of clause 35, wherein, sensors of at least one ring of the two or more rings of sensors are equidistant from a distal end of the mesh of wires.

Clause 36. The mapping overlay of any of clauses 33-36, wherein each of the wires is coated with an electrical insulator.

Clause 37. The mapping overlay of any of clauses 33-37, wherein the wires are braided.

Clause 38. The mapping overlay of any of clauses 33-38, wherein the wires are wound helically.

Clause 39. The mapping overlay of any of clauses 33-39, further comprising a cap coupled to a distal end of the mesh of wires.

Clause 40. The mapping overlay of any of clauses 33-40, wherein the cap comprises an inner cap and an outer cap and the distal end of the mesh of wires is coupled to the inner cap.

Clause 41. The mapping overlay of any of clauses 33-41, wherein the cap comprises a lumen for a guidewire.

Clause 42. The mapping overlay of any of clauses 33-42, further comprising a body comprising one or more inner layers and one or more outer, wherein at least a portion of the mesh of wires is located between the one or more inner layers and the one or more outer layers.

Clause 43. The mapping overlay of any of clauses 33-43, wherein the one or more inner layers and the one or more outer layers comprise a polymer.

Clause 44. The mapping overlay of any of clauses 33-44, wherein the mesh of wires passively expands in response to a force applied thereto by an expanding treatment element of a treatment device.

Clause 45. The mapping overlay of any of clauses 33-45, wherein when the force applied to the mesh of wires by the expanding treatment element dissipates, the mesh of wires retains a deformed shape.

Clause 46. The mapping overlay of any of clauses 33-42 and 45-46, further comprising a body coupled to a proximal portion of the mesh of wires.

Clause 47. The mapping overlay of clause 43, 44, or 47, wherein as the mesh of wires expands in response to the force applied thereto by the expanding treatment element, the body is pulled towards the cap.

Clause 48. The mapping overlay of any of clause 43, 44, 47 and 48, wherein the mesh of wires extends across a length of the body and extends beyond a distal end of the body.

Clause 49. The mapping overlay of clause 43, 44, and 47-49, wherein the mesh of wires extends beyond a proximal end of the body.

Clause 50. The mapping overlay of any of clauses 33-50, wherein the mesh of wires comprises a plurality of conductor wires and a plurality of structural wires that are made from a different material than the plurality of conductor wires, and wherein the plurality of sensors are coupled to the plurality of conductor wires.

Clause 51. The mapping overlay of any of clauses 33-51, wherein the mesh of wires forms a tubular structure.

Clause 52. A treatment device, comprising:
a mesh of wires forming a perimeter of a lumen;
a plurality of sensors coupled to the mesh of wires, and
an expandable treatment element located within the lumen.

Clause 53. The treatment device of clause 53, wherein the expandable treatment element comprises multiple segments.

Clause 54. The treatment device of clause 54, wherein the multiple segments comprise a distal segment and a proximal segment.

Clause 55. The treatment device of any of clauses 53-55, wherein the plurality of sensors comprise at least one of a temperature sensor or a pacing electrode.

Clause 56. The treatment device of any of clauses 53-56, wherein the plurality of sensors are grouped into two or more rings of sensors.

Clause 57. The treatment device of clause 57, wherein, sensors of at least one ring of the two or more rings of sensors are equidistant from a distal end of the mesh of wires.

Clause 58. The treatment device of any of clauses 53-58, wherein each of the wires is coated with an electrical insulator.

Clause 59. The treatment device of any of clauses 53-59, wherein the wires are braided.

Clause 60. The treatment device of any of clauses 53-60, wherein the wires are wound helically.

Clause 61. The treatment device of any of clauses 53-61, further comprising a cap coupled to a distal end of the mesh of wires.

Clause 62. The treatment device of clause 63, wherein the cap comprises an inner cap and an outer cap and the distal end of the mesh of wires is coupled to the inner cap.

Clause 63. The treatment device of any of clauses 62 and 63, wherein the cap comprises a lumen for a guidewire.

Clause 64. The treatment device of any of clauses 53-64, further comprising a body coupled a proximal portion of the mesh of wires.

Clause 65. The treatment device of any of clauses 53-65, further comprising a body comprising one or more inner layers and one or more outer, wherein at least a portion of the mesh of wires is located between the one or more inner layers and the one or more outer layers.

Clause 66. The treatment device of any of clauses 53-66, wherein the one or more inner layers and the one or more outer layers comprise a polymer.

Clause 67. The treatment device of any of clauses 53-67, wherein the mesh of wires passively expands in response to a force applied thereto by an expanding treatment element of a treatment device.

Clause 68. The treatment device of clause 68, wherein when the force applied to the mesh of wires by the expanding treatment element dissipates, the mesh of wires retains a deformed shape.

Clause 69. The treatment device of any of clauses 53-65, 68, and 69, further comprising a body coupled to a proximal portion of the mesh of wires.

Clause 70. The treatment device of clause 66, 67, and 70, wherein as the mesh of wires expands in response to the force applied thereto by the expanding treatment element, the body is pulled towards the cap.

Clause 71. The treatment device of any of clause 66, 67, 70 and 71, wherein the mesh of wires extends across a length of the body and extends beyond a distal end of the body.

Clause 72. The treatment device of clause 66, 67, and 70-72, wherein the mesh of wires extends beyond a proximal end of the body.

Clause 73. The treatment device of clause 73, wherein the mesh of wires comprises a plurality of conductor wires and a plurality of structural wires that are made from a different material than the plurality of conductor wires, and wherein the plurality of sensors are coupled to the plurality of conductor wires.

Clause 74. A mapping overlay of a mapping catheter, the mapping overlay comprising:
a mesh of wires located forming a lumen for a treatment device, the mesh of wires comprising:
a plurality of conductor wires, and
a plurality of structural wires formed of a different material than the plurality of conductor wires, wherein the plurality of conductor wires and the plurality of structural wires are braided to form the mesh of wires;
a plurality of sensors coupled to the plurality of conductor wires;
a cap coupled to a distal end of the mesh of wires; and
a body coupled to the mesh of wires, the body comprising:
one or more inner layers, and
one or more outer layers,
wherein at least a portion of the mesh of wires is located between the one or more inner layers and the one or more outer layers, and the mesh of wires extends past a distal end of the body.

Clause 75. The mapping overlay of clause 75, wherein the plurality of sensors comprise at least one of a temperature sensor or a pacing electrode.

Clause 76. The mapping overlay of any of clauses 75 and 76, wherein the plurality of sensors are grouped into two or more rings of sensors.

Clause 77. The mapping overlay of clause 77, wherein, sensors of at least one ring of the two or more rings of sensors are equidistant from a distal end of the mesh of wires.

Clause 78. The mapping overlay of any of clauses 75-78, wherein each of the plurality of conductor wires is coated with an electrical insulator.

Clause 79. The mapping overlay of any of clauses 75-79, wherein the wires are wound helically.

Clause 80. The mapping overlay of any of clauses 75-80, wherein the cap comprises an inner cap and an outer cap and the distal end of the mesh of wires is coupled to the inner cap.

Clause 81. The mapping overlay of any of clauses 75-81, wherein the cap comprises a lumen for a guidewire.

Clause 82. The mapping overlay of any of clauses 75-82, wherein the one or more inner layers and the one or more outer layers comprise a heat shrunk polymer.

Clause 83. The mapping overlay of any of clauses 75-83, wherein the mesh of wires passively expands in response to a force applied thereto by an expanding treatment element of a treatment device.

Clause 84. The mapping overlay of any of clauses 75-84, wherein when the force applied to the mesh of wires by the expanding treatment element dissipates, the mesh of wires retains a deformed shape.

Clause 85. The mapping overlay of clause 75-85, wherein as the mesh of wires expands in response to the force applied thereto by the expanding treatment element, the body is pulled towards the cap.

Clause 86. The mapping overlay of any of clauses 75-86, wherein the mesh of wires forms a tubular structure.

ADDITIONAL EMBODIMENTS

While the examples above have been described with respect to the treatment of atrial fibrillation, it will be understood that the devices, systems, and methods described herein can be used in a variety of applications where it is desirable to place two medical devices in the same location at different times and the location moves based on an anatomical cycle. For example, a first medical device can be placed at a particular location and its location can be determined with reference to a particular portion of an anatomical cycle, such as end exhalation. The first medical device can be removed and/or moved and a second medical device can be placed in approximately the same location as the first medical device. The location of the second medical device can be determined with respect to the same portion of the anatomical cycle. In this way, a provider can better determine whether the two medical devices are placed at the same location at different times.

Furthermore, reference is made throughout to various catheters that can be used to map and/or treat tissue. It will be understood that the catheters and sheaths described herein can be made of any one or a combination of polymers, including, but not limited to, silicone rubber, nitinol, nylon, polyurethane, polyethylene terephthalate (PET), latex, and thermoplastic elastomers as desired. In addition, the treatment elements and/or balloons described here can be made of polyurethane or other flexible and biocompatible material.

The invention claimed is:

1. A mapping overlay of a mapping catheter, the mapping overlay comprising:
    an elongate, flexible tubular body;
    a mesh of wires forming a tubular sidewall of a cavity configured to self-expand and receive a device therein, the mesh of wires comprising:
        a first plurality of wires, and
        a second plurality of wires formed of a different material than the first plurality of wires, wherein the first plurality of wires and the second plurality of wires are braided to form the mesh of wires, wherein expansion of the mesh of wires is shape set;
    a plurality of electrodes on the first plurality of wires;
    a connector coupled to a distal end of the mesh of wires, the connector comprising a lumen extending through the connector to permit a wire to extend past a distal end of the connector; and
    a catheter body coupled to the mesh of wires, the catheter body comprising:
        one or more inner layers,
        one or more outer layers being coupled to the one or more inner layers such that the one or more outer layers are axially fixed relative to the one or more inner layers, and
        a lumen extending through the catheter body and opening into the cavity to permit the device to be expanded within the cavity;
    wherein at least a portion of the mesh of wires is located between the one or more inner layers and the one or more outer layers, and the mesh of wires extends past a distal end of the catheter body.

2. The mapping overlay of claim 1, wherein the first plurality of wires comprises a plurality of conductor wires, and wherein the second plurality of wires comprises a plurality of structural wires.

3. A catheter configured to deliver electroporation energy to a target tissue, the catheter comprising:
    a catheter body comprising:
        at least one lumen;
        one or more inner layers; and
        one or more outer layers being coupled to the one or more inner layers such that the one or more outer layers are axially fixed relative to the one or more inner layers,
    a mesh of wires configured to extend from a distal end of the catheter body and self-expand to form a cavity, the mesh of wires comprising:
        a first plurality of wires, and
        a second plurality of wires, wherein the first plurality of wires and the second plurality of wires are braided to form the mesh of wires, wherein at least a portion of the mesh of wires is located between the one or more inner layers and the one or more outer layers of the catheter body, and the mesh of wires extends past a distal end of the catheter body;
    an inflatable balloon configured to pass through the at least one lumen into the cavity formed by the mesh of wires; and
    a plurality of electrodes on the first plurality of wires, the plurality of electrodes configured to:
        map a non-target tissue; and
        treat a target tissue region with electrical energy sufficient to cause irreversible electroporation of the target tissue.

4. The catheter of claim 3, wherein the mesh of wires comprises one or more of: steel, polyester-coated copper, nitinol, composite material, platinum, a metal-coated nitinol, tungsten.

5. The catheter of claim 3, wherein the mesh of wires further comprises one or more radiopaque wires.

6. The catheter of claim 3, wherein the first plurality of wires and the second plurality of wires further comprise a biocompatible coating.

7. The catheter of claim 6, wherein the coating is one or more of: polytetrafluoroethylene (PTFE), polyester, and polyimide.

8. The catheter of claim 3, wherein the mesh of wires is shape set.

9. The catheter of claim 8, wherein the shape set mesh of wires is further configured to be expanded by the inflatable balloon.

10. The catheter of claim 3, wherein the mesh of wires further comprises at least one sensor.

11. The catheter of claim 10, wherein the at least one sensor is one of: a radiofrequency electrode, a flow sensor, a temperature sensor, an optical sensor, or a force sensor.

12. The catheter of claim 3, wherein the catheter is configured to be connected to a controller, the controller configured to instruct the plurality of electrodes to one or more of: map the non-target tissue and treat the target tissue.

13. The catheter of claim 3, wherein the plurality of electrodes are further configured to treat the target tissue region by delivering at least one pulse of electrical energy to the target tissue region.

14. A method for ablating tissue, the method comprising:
activating one or more electrodes carried by a self-expanding mesh of wires of a catheter device to stimulate a target or non-target tissue proximate a treatment site, the catheter device further comprising:
  at least one lumen; and
  a catheter body comprising:
    one or more inner layers; and
    one or more outer layers being coupled to the one or more inner layers such that the one or more outer layers are axially fixed relative to the one or more inner layers, wherein at least a portion of the mesh of wires is located between the one or more inner layers and the one or more outer layers, and the mesh of wires extends past a distal end of the catheter body,
determining a location of at least a proximal portion of the non-target tissue based at least in part on said activating;
determining a risk level associated with treatment of the treatment site, prior to commencement of the treatment, based at least in part on the determined location of the proximal portion of the non-target tissue;
inflating a balloon within the self-expanding mesh of wires; and
treating the target tissue at the treatment site with electrical energy via the one or more electrodes based at least in part on the determined risk level, wherein the electrical energy causes irreversible electroporation of the target tissue.

15. The method of claim 14, wherein the target tissue site comprises a cardiac tissue, and the non-target tissue comprises an extracardiac nervous tissue.

16. The method of claim 15, wherein the cardiac tissue comprises a pulmonary vein, and wherein the extracardiac nervous tissue comprises a phrenic nerve.

17. The method of claim 14, wherein the self-expanding mesh of wires comprises one or more of: steel, coated copper polyester, nitinol, composite material, platinum, a coated nitinol, tungsten.

18. The method of claim 14, wherein treating the tissue at the target tissue site comprises delivering at least one pulse of electrical energy to the treatment site.

* * * * *